US012799055B2

(12) United States Patent
Glass et al.

(10) Patent No.: US 12,799,055 B2
(45) Date of Patent: Nov. 17, 2026

(54) PROCESS FOR THE PREPARATION OF A CHIRAL TRIOL

(71) Applicants: Hoffmann-La Roche Inc., Little Falls, NJ (US); Genentech, Inc., South San Francisco, CA (US)

(72) Inventors: Anna-Lena Glass, Bad Saeckingen (DE); Allen Yu Hong, South San Francisco, CA (US); Kurt Puentener, Ueken (CH)

(73) Assignees: Hoffman-La Roche Inc., Little Falls, NJ (US); Genentech, Inc., South San Francisco, CA (US)

( * ) Notice: Subject to any disclaimer, the term of this patent is extended or adjusted under 35 U.S.C. 154(b) by 466 days.

(21) Appl. No.: 18/351,377

(22) Filed: Jul. 12, 2023

(65) Prior Publication Data

US 2024/0018076 A1 Jan. 18, 2024

Related U.S. Application Data

(63) Continuation of application No. PCT/EP2022/050575, filed on Jan. 13, 2022.

(30) Foreign Application Priority Data

Jan. 15, 2021 (EP) .................................... 21151758

(51) Int. Cl.
*C07C 33/26* (2006.01)
*C07C 29/17* (2006.01)

(52) U.S. Cl.
CPC ........ *C07C 29/177* (2013.01); *C07B 2200/07* (2013.01)

(58) Field of Classification Search
CPC .... C07C 29/177; C07C 33/26; C07B 2200/07
See application file for complete search history.

(56) References Cited

U.S. PATENT DOCUMENTS 8,962,839 B2 2/2015 Zhou et al.

FOREIGN PATENT DOCUMENTS

CN 109970795 A 7/2019
JP 2014-501719 A 1/2014

OTHER PUBLICATIONS

Pillay et al. Wacker oxidation methodology for the synthesis of the benzo-fused acetal core of marticin. Tetrahedron 68, 7116-7121. (Year: 2012).*

Herold et al. New Technical Synthesis of Ethyl (R)-2-Hydroxy-4-phenylbutyrate of High Enantiomeric Purity. Tetrahedron 56, 6497-6499. (Year: 2000).*

International Preliminary Report on Patentability—PCT/E P2022/050575 issued Jul. 4, 2023, pp. 1-7.

International Search Report with Written Opinion—PCT/EP2022/050575 mailed May 3, 2022, pp. 1-14.

Lenhart, A. and Chey, W. D., et al., "A Systematic Review of the Effects of Polyols on Gastrointestinal Health and Irritable Bowel Syndrome" Adv. Nutr. 8(4):587-596 (2017).

Ohkuma, T., et al., "Asymmetric Hydrogenation of alpha-Hydroxy Ketones Catalyzed by MsDPEN-Cp*Ir(III) Complex" Org. Lett. 9(13):2565-2567 (2007).

Ticozzi, C., et al., "Synthesis of a bifunctional 2, 4-dihydroxy five-carbon synthon. Enantiomerically pure [Delta] 2-isoxazolines by chromatographic resolution" Tetrahedron Lett. 35(40):7421-7424 (1994).

Yang, X-H., et al., "Catalytic Asymmetric Hydrogenation of δ-Ketoesters: Highly Efficient Approach to Chiral 1,5Diols" Angew. Chem., Int. Ed. 52:7833-7836 (2013).

Liu et al., "Asymmetric Hydrogenation of Tetrasubstituted Cyclic Enones to Chiral Cycloalkanols with Three Contiguous Stereocenters" Org. Lett. 17:3231-3234 ( 2017).

Harvey et al., "Stereospecific Hydrogenolysis of Benzylic Alcohols over Pd/C" J Clin Oncol 85:7611-7619 ( 2020).

* cited by examiner

*Primary Examiner* — Sikarl A Witherspoon
(74) *Attorney, Agent, or Firm* — Jelena Libby

(57) ABSTRACT

The invention comprises a process for the preparation of a chiral triol of formula I

I

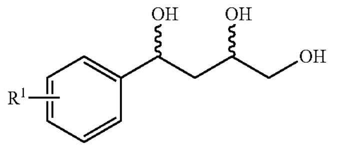

wherein, $R^1$ is hydrogen or halogen
by way of an asymmetric hydrogenation of a ketone compound of formula IIa IIa

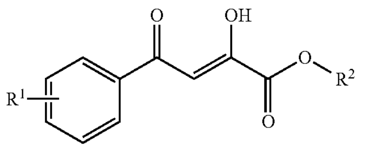

wherein, $R^1$ is hydrogen or halogen and $R^2$ is $C_{1-6}$-alkyl; with hydrogen in the presence of an iridium spiro-pyridylamidophosphine catalyst (Ir-SpiroPAP catalyst). The chiral triols of formula I are versatile building blocks for the preparation of various pharmaceutically active drug substances such as for instance for statins.

25 Claims, No Drawings

PROCESS FOR THE PREPARATION OF A CHIRAL TRIOL

The invention relates to a process for the preparation of the chiral triol of the formula I

I

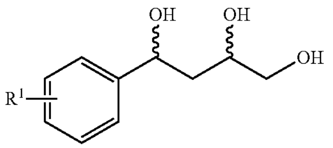

wherein $R^1$ is hydrogen or halogen and denotes either a dashed bond (a) or a wedged bond (b)

a)  b) .

Chiral triols are versatile building blocks for the preparation of various pharmaceutically active drug substances such as for instance for statin drugs (A. Lenhart, W. D. Chey "Adv. Nutr. 2017, 8(4), 587-596).

The object of the present invention was to provide a process which allows the preparation of the chiral triol in a scalable manner with high enantiomeric purity and yield.

The object could be reached with the process for the preparation of the chiral triol of formula I

I

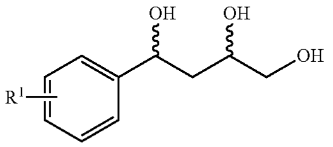

wherein $R^1$ is hydrogen or halogen and denotes either a dashed bond (a) or a wedged bond (b)

a)  b) .

and which comprises the asymmetric hydrogenation of a ketone compound of formula IIa IIa

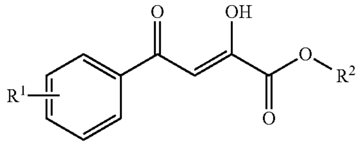

wherein $R^1$ is hydrogen or halogen and $R^2$ is $C_{1-6}$-alkyl;

with hydrogen in the presence of an iridium spiro-pyridylamidophosphine catalyst (Ir-SpiroPAP catalyst) of the formula IIIa or IIIb, or enantiomers thereof IIIa

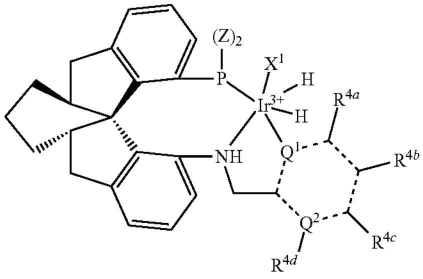

IIIb

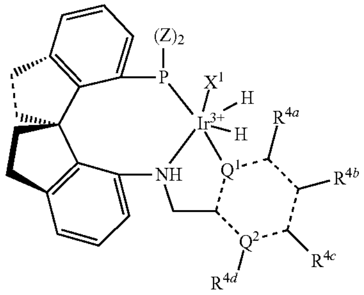

wherein $R^{4a}$, $R^{4b}$, $R^{4c}$ and $R^{4d}$ independently of each other are hydrogen or $C_{1-6}$-alkyl;

the dotted ring signifies an aromatic ring when $Q^1$ is nitrogen and $Q^2$ is carbon and the dotted ring signifies a cycloalkane ring wherein $Q^1$ and $Q^2$ are sulfur;

$X^1$ is either a coordinated ligand or a counter anion selected from halogen, $C_{1-6}$-alkoxy, tetrahalogenoborate, hexahalogenoborate, tetrakis (3,5-bis(trihalogeno-$C_{1-6}$-alkyl) phenyl)borate, acetylacetonate, hexahalogenophosphate, p-tolylsulfonate (OTs) or trihalogeno methanesulfonate and Z is phenyl, optionally substituted by one or more groups selected from $C_{1-8}$-alkyl, $C_{1-8}$-halogenalkyl or phenyl; $C_{3-8}$-cycloalkyl, optionally substituted by one or more $C_{1-8}$-alkyl groups or di-$C_{1-8}$-alkyl phosphinyl.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

The term "chiral" denotes the ability of non-superimposability with the mirror image, while the term "achiral" refers to embodiments which are superimposable with their mirror image. Chiral molecules are optically active, i.e., they have the ability to rotate the plane of plane-polarized light. Whenever a chiral center is present in a chemical structure, it is intended that all stereoisomers associated with that chiral center are encompassed by the present invention.

The term "chiral" signifies that the molecule can exist in the form of optically pure enantiomers, mixtures of enantiomers, optically pure diastereoisomers or mixtures of diastereoisomers.

In a preferred embodiment of the invention the term "chiral" denotes optically pure enantiomers or optically pure diastereoisomers.

The term "stereoisomer" denotes a compound that possesses identical molecular connectivity and bond multiplicity, but which differs in the arrangement of its atoms in space.

The term "diastereomer" denotes a stereoisomer with two or more centers of chirality and whose molecules are not mirror images of one another. Diastereomers may have different physical properties, e.g. melting points, boiling points, spectral properties, and reactivities.

The term "enantiomers" denotes two stereoisomers of a compound which are non-superimposable mirror images of one another.

In the structural formula presented herein a dashed bond (a) denotes that the substituent is below the plane of the paper and a wedged bond (b) denotes that the substituent is above the plane of the paper.

a)  b)

The spiral bond (c) denotes both options i.e. either a dashed bond (a) or a wedged bond (b).

c)

The term "$C_{1-8}$-alkyl" denotes a monovalent linear or branched saturated hydrocarbon group of 1 to 8 carbon atoms. Examples of $C_{1-8}$-alkyl include methyl, ethyl, propyl, isopropyl, n-butyl, isobutyl, sec-butyl, tert-butyl or pentyl, hexyl, heptyl or octyl with its isomers. Preferably the term denotes a $C_{1-6}$-alkyl group.

The term "$C_{3-8}$-cycloalkyl" denotes a saturated carbocycle of 3 to 8 carbon atoms. Examples of $C_{3-8}$-cycloalkyl include cyclopropyl, cyclobutyl, cyclopentyl, cyclohexyl, cycloheptyl and cyclooctyl with its isomers. Preferably the term encompasses $C_{4-7}$-cycloalkyl, more preferably cyclpentyl and cyclohexyl.

The term "$C_{1-6}$-alkoxy" denotes a monovalent linear or branched saturated hydrocarbon group of 1 to 6 carbon atoms attached to an oxygen atom. Examples of $C_{1-6}$-alkoxy include methoxy, ethoxy, propoxy, isopropoxy, n-butoxy, iso-butoxy, sec-butoxy, tert-butoxy, or pentoxy or hexoxy with its isomers. Preferably the term denotes a $C_{1-4}$-alkoxy group, more preferably the methoxy group.

The term "halogen" denotes fluoro, chloro, bromo, or iodo.

The term "$C_{1-8}$-halogenalkyl" denotes a monovalent linear or branched saturated hydrocarbon group of 1 to 8 carbon atoms which is substituted by one or more halogen atoms. Preferably the term denotes $C_{1-4}$-halogenalkyl, more preferably a methyl group which is substituted with one or more halogen atoms such as trifluoromethyl.

The ketone of formula IIa may occur in the mesomeric structures outlined in the scheme below. For the sake of clarity the formula IIa is consistently used throughout this description.

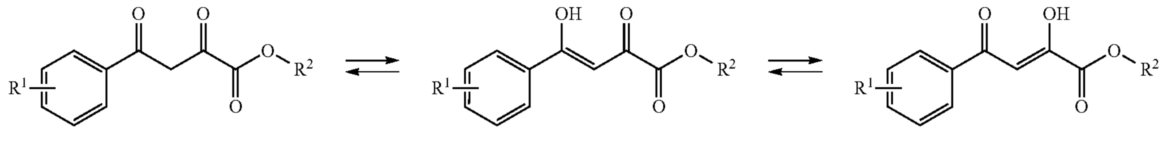

IIa

The process of the present invention can be illustrated with the scheme 1 below

Scheme 1

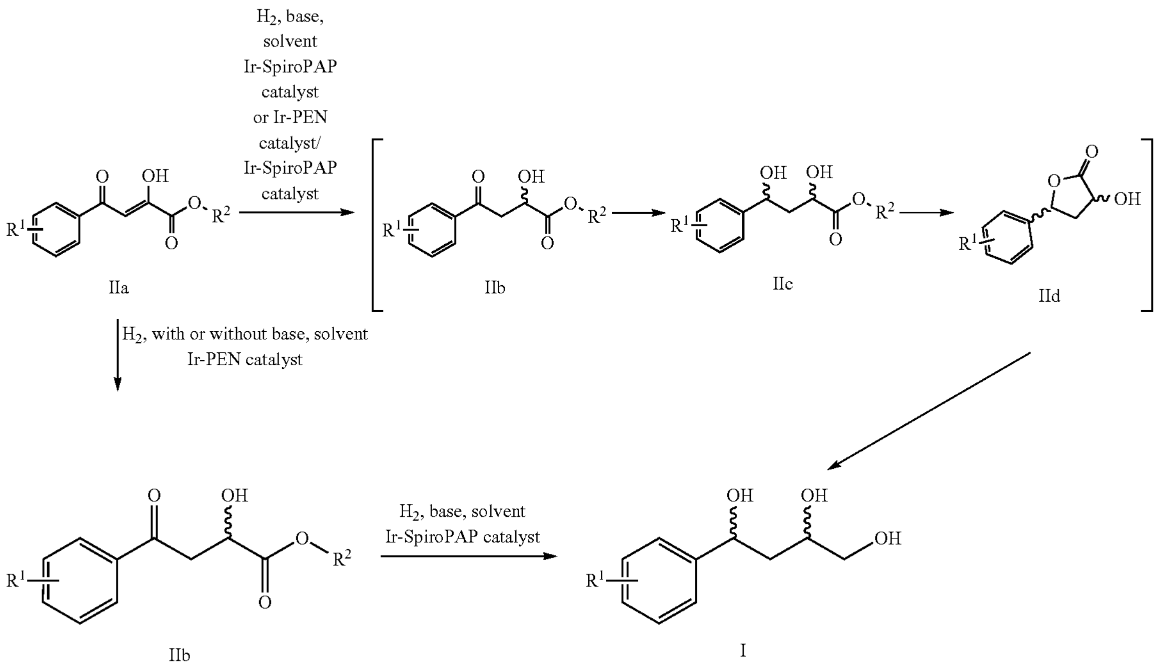

IIa IIb IIc IId IIb I and comprises the following various principal embodiments for the preparation of the chiral triol of formula I.

a) The asymmetric hydrogenation of the ketone of formula IIa in the sole presence of an Ir-SpiroPAP catalyst.

b) The asymmetric hydrogenation of the ketone of formula IIa in the presence of an in situ formed Ir-SpiroPAP catalyst.

c) The asymmetric hydrogenation of the ketone of formula IIa in the sole presence of an Ir-PEN catalyst to form the ketone of formula IIb and its subsequent asymmetric hydrogenation to the chiral triol of formula I in the presence of the Ir-SpiroPAP catalyst.

d) The asymmetric hydrogenation of the ketone of formula IIa in the presence of a mixture of an Ir-SpiroPAP catalyst and an Ir-PEN catalyst.

$R^1$ can be in the ortho-, meta- or para-position of the phenyl ring, but preferably $R^1$ is in the para-position of the phenyl ring.

In a further preferred embodiment of the present invention the chiral triol has the formula Ib Ib

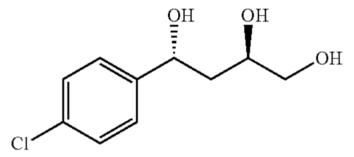

Scheme 2 illustrates a preferred embodiment of the invention.

Scheme 2

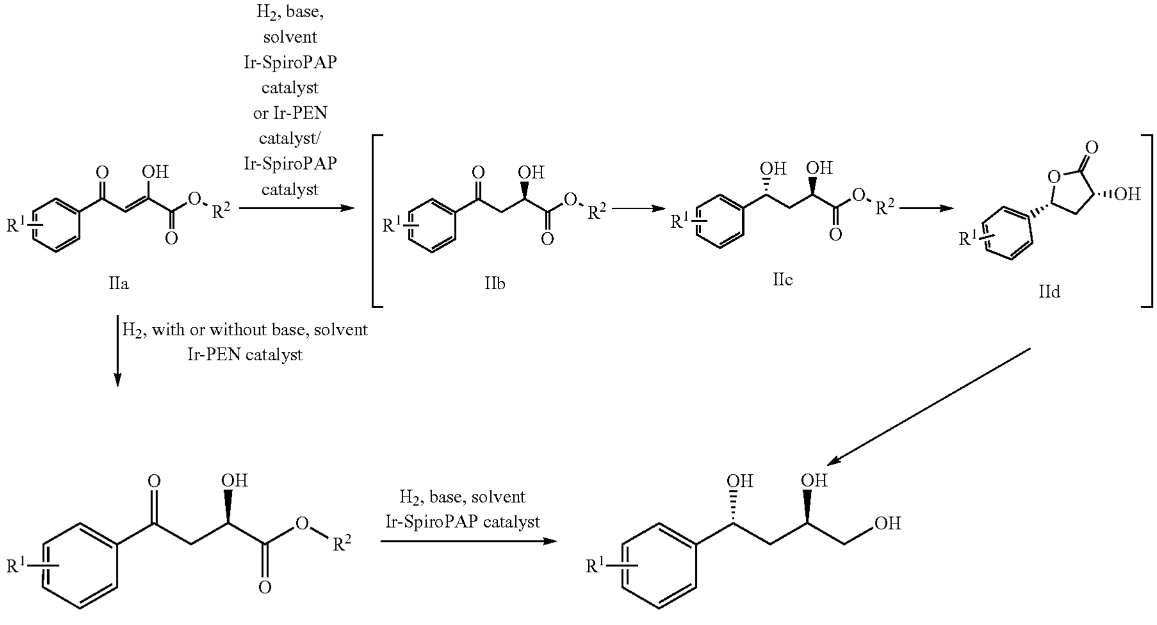

IIa IIb IIc IId IIb I e) The asymmetric hydrogenation of either intermediate IIb, IIc or IId in presence of an Ir-SpiroPAP catalyst.

The embodiments a) to d) are preferred, more preferred are the embodiments a), b) and d) and embodiment d) is most preferred.

In a preferred embodiment of the present invention the chiral triol has the formula Ia Ia

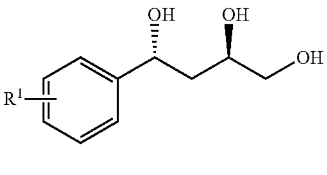

wherein $R^1$ is as above, but preferably stands for halogen, more preferably for chlorine.

a) the Asymmetric Hydrogenation of the Ketone of Formula IIa in the Sole Presence of an Ir-SpiroPAP Catalyst The iridium spiro-pyridylamidophosphine catalyst (Ir-SpiroPAP catalyst) are of the formula IIIa or IIIb, or enantiomers thereof IIIa

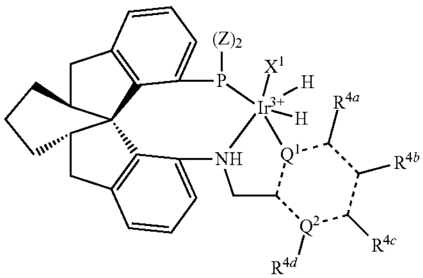

-continued

IIIb

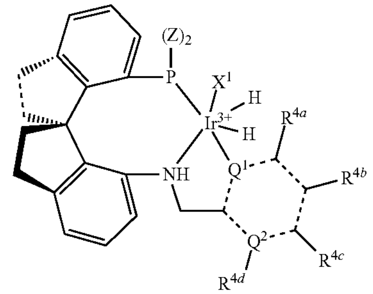

wherein $R^{4a}$, $R^{4b}$, $R^{4c}$ and $R^{4d}$ independently of each other are hydrogen or $C_{1-6}$-alkyl;

the dotted ring signifies an aromatic ring when $Q^1$ is nitrogen and $Q^2$ is carbon and the dotted ring signifies a cycloalkane ring wherein $Q^1$ and $Q^2$ are sulfur;

$X^1$ is either a coordinated ligand or a counter anion selected from halogen, $C_{1-6}$-alkoxy, tetrahalogenoborate, hexahalogenoborate, tetrakis (3,5-bis(trihalogeno-$C_{1-6}$-alkyl)phenyl)borate, acetylacetonate, hexahalogenophosphate, p-tolylsulfonate (OTs) or trihalogeno methanesulfonate and Z is phenyl, optionally substituted by one or more groups selected from $C_{1-8}$-alkyl, $C_1$-s-halogenalkyl or phenyl; $C_{3-8}$-cycloalkyl, optionally substituted by one or more $C_{1-8}$-alkyl groups or di-$C_{1-8}$-alkyl phosphinyl.

In a preferred embodiment $R^{4a}$, $R^{4b}$, $R^{4c}$ and $R^{4d}$ independently of each other are hydrogen or $C_{1-4}$-alkyl;

the dotted ring signifies an aromatic ring when $Q^1$ is nitrogen and $Q^2$ is carbon and the dotted ring signifies a cycloalkane ring wherein $Q^1$ and $Q^2$ are sulfur;

$X^1$ is either a coordinated ligand or a counter anion selected from halogen, methoxy, tetrafluoroborate (BF4), hexafluoroborate (BF6), tetrakis(3,5-bis(trifluoromethyl) phenyl)borate (barf), acetylacetonate (acac), hexafluorophosphate (PF6), p-tolylsulfonate (OTs) or trifluoromethanesulfonate (OTf) and;

Z is phenyl, optionally substituted by one or more groups selected from $C_{1-6}$-alkyl, $C_{1-4}$-halogenalkyl or phenyl or is $C_{4-7}$-cycloalkyl.

In a further preferred embodiment $R^{4a}$, $R^{4b}$, $R^{4c}$ and $R^{4d}$ independently of each other are hydrogen or $C_{1-4}$-alkyl;

the dotted ring signifies an aromatic ring when $Q^1$ is nitrogen and $Q^2$ is carbon and the dotted ring signifies a cycloalkane ring wherein $Q^1$ and $Q^2$ are sulfur;

$X^1$ is halogen;

Z is phenyl, optionally substituted by one or two groups selected from $C_{1-6}$-alkyl, $C_{1-4}$-halogenalkyl or phenyl or is cyclopentyl or cyclohexyl.

In a further preferred embodiment the iridium spiro-pyridylamidophosphine catalyst (Ir-SpiroPAP catalyst) are selected from the compounds IIIc

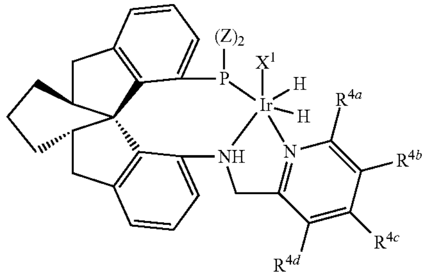

IIId

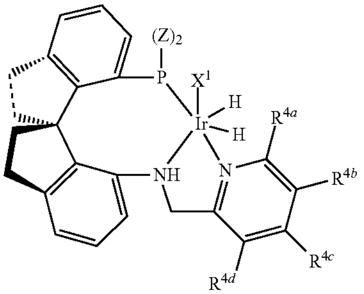

IIIe

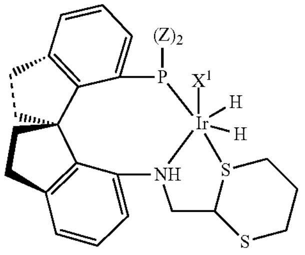

wherein;

$R^{4a}$, $R^{4b}$, $R^{4c}$ and $R^{4d}$ independently of each other are hydrogen or $C_{1-4}$-alkyl;

$X^1$ is halogen;

Z is phenyl optionally substituted by one or two groups selected from $C_{1-6}$-alkyl, $C_{1-4}$-halogenalkyl or phenyl or is cyclopentyl or cyclohexyl.

In a further preferred embodiment the iridium spiro-pyridylamidophosphine catalyst (Ir-SpiroPAP catalyst) is selected from the compound IIId

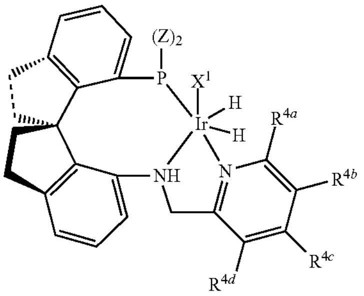

wherein $R^{4a}$, $R^{4b}$, $R^{4c}$ and $R^{4d}$ independently of each other are hydrogen or $C_{1-4}$-alkyl;

$X^1$ is a ligand selected from halogen;

Z is phenyl, optionally substituted by one or two groups selected from $C_{1-6}$-alkyl, $C_{1-4}$-halogenalkyl or phenyl or is cyclopentyl or cyclohexyl, more preferably, $R^{4a}$, $R^{4b}$, $R^{4c}$ is hydrogen and $R^{4d}$ is methyl;

$X^1$ is chlorine and

Z is phenyl, 3,5-dimetylphenyl, 3,5-di-tert-butyl phenyl, 3,5-di-tert-pentyl phenyl, 3,5-diphenyl phenyl, 4-phenyl phenyl, 3,5-di-trifluoromethyl phenyl, cyclohexyl or cyclopentyl.

Suitable catalysts are typically commercially available e.g. from Jiuzhou Pharma in China.

The asymmetric hydrogenation can be performed in the presence of suitable organic solvent and a base at a hydrogen pressure of 5 bar to 100 bar, preferably of 30 bar to 70 bar and at a reaction temperature of 10° C. to 90° C., preferably of 20° C. to 40° C.

The organic solvent can be selected from aliphatic alcohols selected from methanol, ethanol, isopropanol, tert-amylalcohol, from halogen substituted alcohols like trifluoroethanol, from haloalkanes like dichloromethane, from ethers like tetrahydrofuran or dioxane or from aromatic solvents like toluene or mixtures thereof. Also suited are mixtures of aliphatic alcohols such as methanol or ethanol with water or with dioxane. The preferred solvent is methanol or ethanol, even more preferred ethanol.

Suitable bases are inorganic bases selected from alkali or earth alkali—carbonates or—hydrogen carbonates or phosphates or hydrogenphosphates or dihydrogenphosphates or acetates or formates or organic bases selected from amines, alkali alcoholates or amidines. Organic bases are usually preferred. Typical representatives of organic bases are potassium tert-butylate or 1,8-Diazabicyclo[5.4.0]undec-7-ene (DBU), 1,4-Diazabicyclo(2.2.2)octane (DABCO) and 7-Methyl-1,5,7-triazabicyclo[4.4.0]dec-5-ene (MTBD), most preferred is DBU.

A substrate to catalyst ratio can expediently be chosen in a range of 100 to 10,000, preferably in a range of 1000 to 5000.

The chiral triol of formula I can be separated from the reaction mixture by evaporation of the solvent. Subsequent crystallization in a suitable solvent, typically in ketones like methyl isobutyl ketone or esters like isopropyl acetate renders the chiral triol of formula I in good yields, high purity and high enantiomeric excess.

b) the Asymmetric Hydrogenation of the Ketone of Formula IIa in the Presence of an In Situ Formed Ir-SpiroPAP Catalyst.

In another embodiment the iridium spiro-pyridylamidophosphine catalyst (Ir-SpiroPAP catalyst) of formula IIIa or IIIb may be prepared in situ in the course of the asymmetric hydrogenation reaction by bringing together a suitable Iridium-pre catalyst complex with a spiro-pyridylamidophosphine ligand of the formula VIa

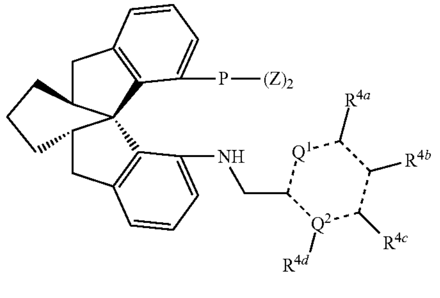

-continued

VIb

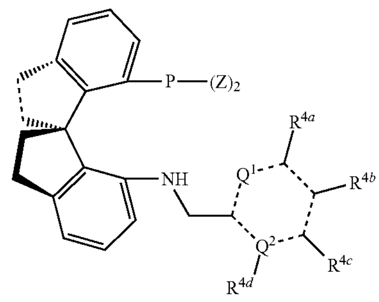

wherein $R^{4a}$, $R^{4b}$, $R^{4c}$ and $R^{4d}$, $Q^1$ and $Q^2$ and Z have the meanings as outlined above. Suitable Iridium-pre catalyst complex compounds are commercially available e.g. from Sigma Aldrich and can be selected e.g. from $[Ir(cod)_2]BF_4$, $[IrCl(COD)]_2$, [Ir(acac)(COD)], $[Ir(OMe)(COD)]_2$, $[Ir(cod)_2]BARF$, $[Ir(cod)_2]PF6$, wherein cod or COD has the meaning of cyclooctadiene, acac the meaning of acetylacetonate, BARF the meaning of tetrakis(3,5-bis(trifluoromethyl)phenyl)borate and OMe the meaning of methoxy.

Preferred Iridium-pre catalyst complex compound is [IrCl(COD)]2.

Usually the iridium-pre catalyst complex compound and the spiro-pyridylamidophosphine ligand are typically mixed in the presence of the organic solvent and the base mentioned under embodiment a).

The substrate to Iridium ratio as a rule is adjusted between 100 and 10000, preferably between 1000 and 5000. The substrate to ligand ratio as a rule is adjusted between 0.5 and 1.5, preferably between 0.9 and 1.1.

The asymmetric hydrogenation conditions and the isolation of the chiral triol of formula I can otherwise be chosen as for the process of embodiment a). Also the preferred embodiments outlined in embodiment a) apply likewise.

c) the Asymmetric Hydrogenation of the Ketone of Formula IIa to the Ketone of Formula IIb in the Sole Presence of an Ir-PEN Catalyst and the Subsequent Asymmetric Hydrogenation to the Chiral Triol of Formula I in the Presence of the Ir-SpiroPAP Catalyst.

The iridium-phenylendiamine catalyst (Ir-PEN catalyst) are of the formula IVa or IVb, or enantiomers thereof IVa

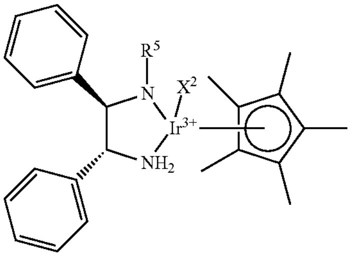

-continued

IVb

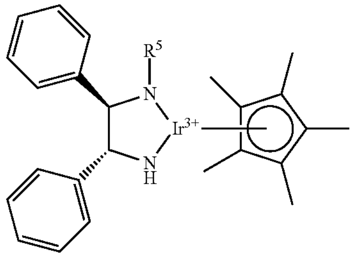

wherein, $R^5$ is $C_{1-6}$-alkylsulfonyl wherein the alkyl group is optionally substituted with one or more halogen atoms; with a 7,7-dimethyl-2-oxobicyclo[2.2.1] heptane-1-yl group or phenyl sulfonyl, wherein the phenyl group is optionally substituted by one or more $C_1$. 6-alkyl groups and $X^2$ is either a coordinated ligand or a counter anion selected from a $C_{1-6}$-alkylsulfonyloxy group which is optionally substituted with one or more halogen, atoms; from halogen, $C_{1-6}$-alkoxy, tetrahalogenoborate, hexahalogenoborate, tetrakis(3,5-bis(trihalogeno-$C_{1-6}$-alkyl)phenyl)borate, acetylacetonate, hexahalogenophosphine, p-tolylsulfonate (OTs) or trihalogenomethanesulfonate;

In a preferred embodiment the iridium-phenylendiamine catalyst (Ir-PEN catalyst) are of the formula IVa or IVb, or enantiomers thereof, wherein $R^5$ is methylsulfonyl, trifluoromethylsulfonyl, 7,7-dimethyl-2-oxobicyclo[2.2.1] heptane-1-yl; tolylsulfonyl or 1,3,5-tri-i-propylphenyl sulfonyl;

$X^2$ is either a coordinated ligand or a counter anion selected from a methylsulfonyloxy group which is optionally substituted with one or more fluoro atoms; from halogen, methoxy, tetrafluoroborate (BF4), hexafluoroborate (BF6), tetrakis(3,5-bis(trifluoromethyl)phenyl)borate (barf), acetylacetonate (acac), hexafluorophosphate (PF6), p-tolylsulfonate (OTs) or trifluoromethanesulfonate (OTf;

In a further preferred embodiment the iridium-phenylendiamine catalyst (Ir-PEN catalyst) are of the formula IVa, or enantiomers thereof, wherein, $R^5$ is methylsulfonyl, trifluoromethylsulfonyl, 7,7-dimethyl-2-oxobicyclo[2.2.1]heptane-1-yl; tolylsulfonyl or 1,3,5-tri-i-propylphenyl sulfonyl;

$X^2$ is a trifluoromethylsulfonyl oxy group;

In a further preferred embodiment the iridium-phenylendiamine catalyst (Ir-PEN catalyst) are of the formula IVb, or enantiomers thereof, wherein, $R^5$ is methylsulfonyl, trifluoromethylsulfonyl, 7,7-dimethyl-2-oxobicyclo[2.2.1]heptane-1-yl; tolylsulfonyl or 1,3,5-tri-i-propylphenyl sulfonyl.

In a further preferred embodiment the iridium-phenylendiamine catalyst (Ir-PEN catalyst) are selected from compounds of the formula IVc and IVd IVc

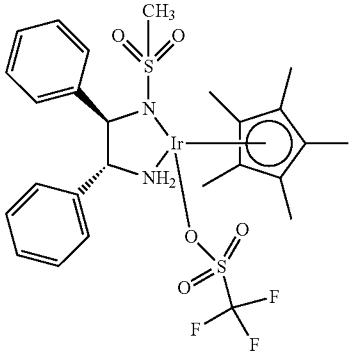

IVd

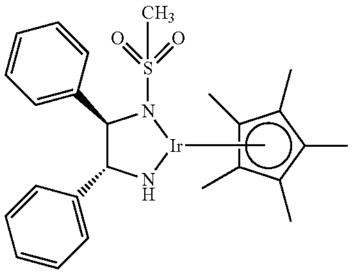

The asymmetric hydrogenation for the formation of the ketone of formula IIb of can be performed in the presence of suitable organic solvent at a hydrogen pressure of 5 bar to 100 bar, preferably of 30 bar to 70 bar and at a reaction temperature of 10° C. to 90° C., preferably of 20° C. to 40° C.

The organic solvent can be selected from aliphatic alcohols selected from methanol, ethanol, isopropanol, tert-amylalcohol, from halogen substituted alcohols like trifluoroethanol, from haloalkanes like dichloromethane, from ethers like tetrahydrofuran or dioxane or from aromatic solvents like toluene or mixtures thereof. Also suited are mixtures of aliphatic alcohols such as methanol or ethanol with water or with dioxane. The preferred solvent is methanol or ethanol, even more preferred ethanol.

The reaction can be performed without the presence of a base.

However, bases are tolerated. Suitable bases are inorganic bases selected from alkali or earth alkali—carbonates or—hydrogen carbonates or phosphates or hydrogenphosphates or dihydrogenphosphates or acetates or formates or organic bases selected from amines, alkali alcoholates or amidines. Organic bases are usually preferred. Typical representatives of organic bases are potassium tert-butylate or 1,8-Diazabicyclo[5.4.0]undec-7-ene (DBU), 1,4-Diazabicyclo(2.2.2)octane (DABCO) and 7-Methyl-1,5,7-triazabicyclo[4.4.0]dec-5-ene (MTBD), most preferred is DBU.

A substrate to catalyst ratio can expediently be chosen in a range of 100 to 10000, preferably in a range of 500 to 1000.

The ketone of formula IIb can be separated from the reaction mixture by evaporation of the solvent. Subsequent crystallization in a suitable solvent, typically in an aliphatic alcohol like i-propanol renders the ketone of formula IIb in good yields, high purity and high enantiomeric excess. Alternatively the ketone of formula IIb is not isolated and is further hydrogenated to the chiral triol of formula I in the presence of the Ir-SpiroPAP catalyst.

The subsequent asymmetric hydrogenation can take place in the same manner as described in embodiment a)

d) the Asymmetric Hydrogenation of the Ketone of Formula IIa in the Presence of a Mixture of an Ir-SpiroPAP Catalyst and an Ir-PEN Catalyst.

In this embodiment the asymmetric hydrogenation is performed in the presence of a mixture of the Ir-SpiroPAP catalyst and an Ir-PEN catalyst.

Typically the Ir-PEN catalyst catalyzes the first step of the reaction i.e. the transformation to the ketone of formula IIb faster and with a higher chiral selectivity than the Ir-SpiroPAP catalyst.

Therefore, regarding catalyst concentration of the two catalysts a higher Ir-PEN catalyst concentration is as a rule applied.

The substrate to Ir-PEN catalyst ratio can therefore expediently be chosen in a range of 100 to 10000 preferably in a range of 500 to 1000.

The substrate to Ir-Spiro-PAP catalyst ratio can expediently be chosen in a range of 100 to 10000, preferably in a range of 2500 to 7500.

The asymmetric hydrogenation can be performed in the presence of suitable organic solvent and a base at a hydrogen pressure of 5 bar to 100 bar, preferably of 30 bar to 70 bar and at a reaction temperature of 10° C. to 90° C., preferably of 20° C. to 40° C.

The organic solvent can be selected from aliphatic alcohols selected from methanol, ethanol, isopropanol, tert-amylalcohol, from halogen substituted alcohols like trifluoroethanol, from haloalkanes like dichloromethane, from ethers like tetrahydrofuran or dioxane or from aromatic solvents like toluene or mixtures thereof. Also suited are mixtures of aliphatic alcohols such as methanol or ethanol with water or with dioxane. The preferred solvent is methanol or ethanol, even more preferred ethanol.

Suitable bases are inorganic bases selected from alkali or earth alkali—carbonates or—hydrogen carbonates or phosphates or hydrogenphosphates or dihydrogenphosphates or acetates or formates or organic bases selected from amines, alkali alcoholates or amidines. Organic bases are usually preferred. Typical representatives of organic bases are potassium tert-butylate or 1,8-Diazabicyclo[5.4.0]undec-7-ene (DBU), 1,4-Diazabicyclo(2.2.2)octane (DABCO) and 7-Methyl-1,5,7-triazabicyclo[4.4.0]dec-5-ene (MTBD), most preferred is DBU.

The chiral triol of formula I can be separated from the reaction mixture by evaporation of the solvent. Subsequent crystallization in a suitable solvent, typically in ketones like methyl isobutyl ketone or esters like isopropyl acetate renders the chiral triol of formula I in good yields, high purity and high enantiomeric excess.

e) the Asymmetric Hydrogenation of Intermediate IIb, IIc or IId. In the Sole Presence of an Ir-SpiroPAP Catalyst The intermediates IIb, IIc or IId typically need not to be isolated and can directly be converted to the desired chiral triol of formula I.

Intermediate IIb can be prepared and isolated in accordance with embodiment c).

Also intermediate IIc or IId can in principle be isolated by interrupting the hydrogenation at the appropriate stage and individually be subjected to the asymmetric hydrogenation with either the Ir-Spiro PAP catalyst alone or in the presence of a mixture of an Ir-SpiroPAP catalyst and an Ir-PEN catalyst. The reaction conditions as described in the previous embodiments can likewise be applied.

As outlined above the embodiments a) to d) are preferred, more preferred are the embodiments a), b) and d) and embodiment d) is most preferred.

EXAMPLES

Abbreviations

| | |
|---|---|
| EtOH | Ethanol |
| $iPr_2O$ | Diisopropyl ether |
| MeOH | Methanol |
| DCM | Dichloromethane |
| Dioxane | 1,4-Dioxane |
| iPrOH | 2-Propanol |
| iPrOAc | Isopropyl acetate |
| tAmOH | tert-Amylalcohol |
| TFE | Trifluoroethanol |
| THF | Tetrahydrofuran |
| DBU | Diazabicycloundecene |
| DABCO | 1,4-Diazabicyclo(2.2.2)octane |
| MTBD | Triazabicyclodecene |
| DBN | 1,5-Diazabicyclo(4.3.0)non-5-ene |
| BIPY | Biypridine |
| COD | Cyclooctadiene |
| rt | Room temperature |
| IPC | In process control |
| T | Temperature |
| P | Hydrogen pressure |
| eq | Equivalent |
| rct | Reaction time |
| con | Conversion |
| exp | Experiment |
| S/C | Substrate-to-Catalyst ratio |
| S/L | Substrate-to-Ligand ratio |
| S/B | Substrate-to-Base ratio |
| S/Ir | Substrate-to-Iridium ratio |

| | |
|---|---|
| 1 | 4-(4-Chlorophenyl)-2-hydroxy-4-keto-butyric-2-en-acid ethyl ester (Note: 1H-NMR spectra data of 1 in D6-EtOH or $CD_2Cl_2$ confirmed the structure to be assigned as: 4-(4-chlorophenyl)-2-hydroxy-4-keto-butyric-2-en-acid ethyl ester. No hint was found for the presence of 4-(4-Chlorophenyl)-2-diketo-butyric acid ethyl ester) |
| (R)-3 = (2R)-3 | (2R)-4-(4-Chlorophenyl)-2-hydroxy-4-keto-butyric acid ethyl ester |
| (R,R)-4 = trans-(2R, 4R)-4 | (2R,4R)-4-(4-Chlorophenyl)-2,4-dihydroxy-butyric acid ethyl ester |
| trans-4 | mix of (R,R)-4 and (S,S)-4 |
| cis-4 | mix of (R,S)-4 and (S,R)-4 |
| (R,R)-5 = cis-(3R,5R)-5 | (3R,5R)-5-(4-Chlorophenyl)-3-hydroxy-butyrolactone |
| cis-5 | mix of (R,R)-5 and (S,S)-5 |
| trans-5 | mix of (R,S)-5 and (S,R)-5 |

-continued

| | |
|---|---|
| (R,R)-6 = trans-(2R, 4R)-6 | (2R,4R)-4-(4-Chlorophenyl)-butane-1,2,4-triol |
| trans-6 | mix of (R,R)-6 and (S,S)-6 |
| cis-6 | mix of (R,S)-6 and (S,R)-6 |
| 7 | 4-(Phenyl)-2-hydroxy-4-keto-butyric-2-en-acid ethyl ester (Note: 1H-NMR spectra data of 7 in $CD_2Cl_2$ confirmed the structure to be assigned as: 4-(Phenyl)-2-hydroxy-4-keto-butyric-2-en-acid ethyl ester. No hint was found for the presence of 4-(Phenyl)-2-diketo-butyric acid ethyl ester) |
| (R,R)-8 = trans-(2R, 4R)-8 | (2R,4R)-4-(Phenyl)-butane-1,2,4-triol |
| trans-8 | mix of (R,R)-8 and (S,S)-8 |
| cis-8 | mix of (R,S)-8 and (S,R)-8 |

Scheme 3a

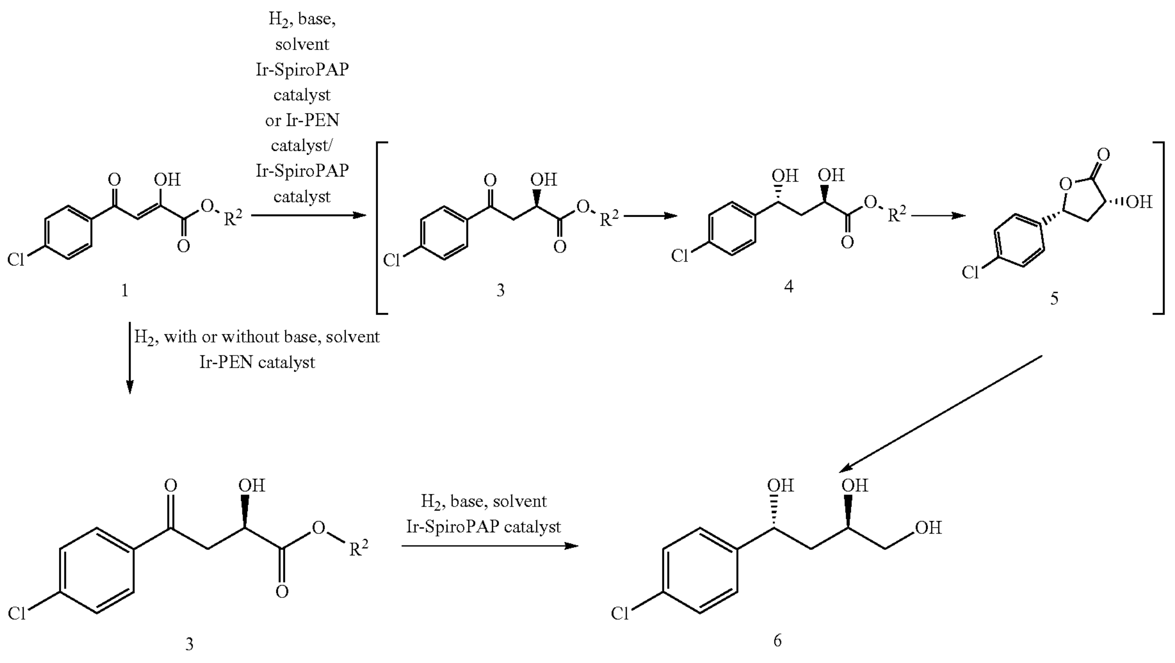

$R^2$ = ethyl

Scheme 3b

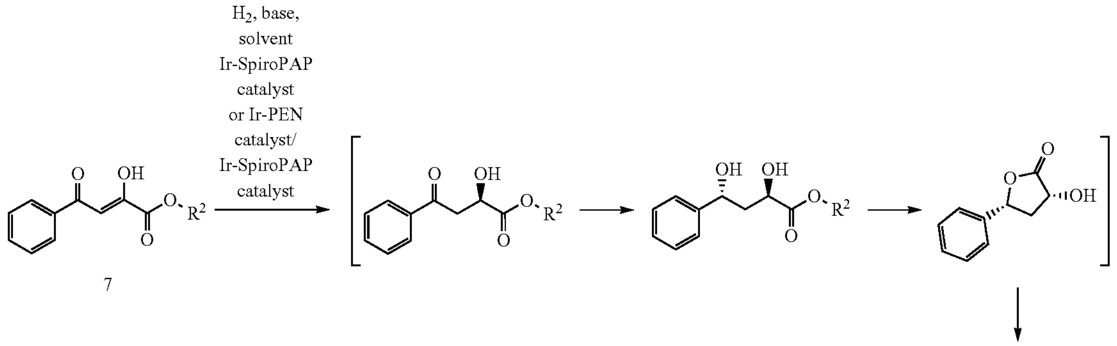

7

-continued

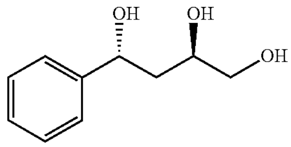

8

$R^2$ = ethyl

Pre-Catalysts, Catalyst and Ligands:

627-630 and 6051-6056 were prepared according to T. Ohjuma et al. *Organic Letters,* 2007, 9, 2565. All other (pre-) catalysts and ligands were commercially available e.g. from Strem, Sigma Aldrich, Jiuzhou Pharma.

| (Pre-) Catalysts and Ligands | | |
|---|---|---|
| Number | Abbreviation | Structure |
| 627 | [Ir(cp*)((S,S)-Ms-DPEN-2H)]<br>CAS No 937378-51-3 | 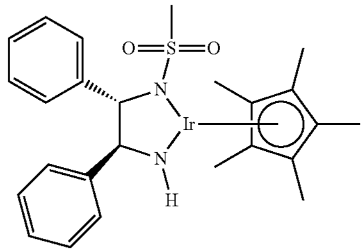 |
| 628 | [Ir(cp*)((S,S)-Ms-DPEN-H)(OTf)]<br>CAS No 917756-11-7 | 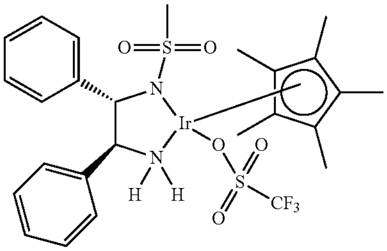 |
| 629 | [Ir(cp*)((R,R)-Ms-DPEN-2H)]<br>CAS No 1263000-75-4 | 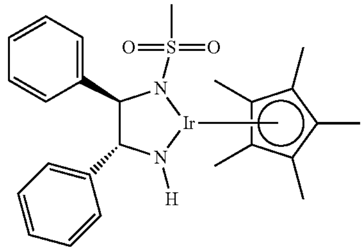 |
| 630 | [Ir(cp*)((R,R)-Ms-DPEN-H))(OTf)]<br>CAS No 1201686-18-1 | 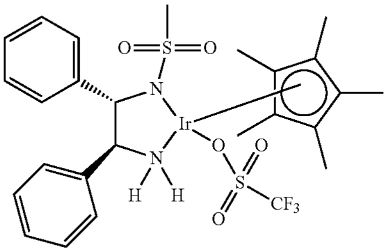 |

-continued
| (Pre-) Catalysts and Ligands | | |
|---|---|---|
| Number | Abbreviation | Structure |
| 6051 | [Ir(cp*)((R,R)-Ts-DPEN-2H)]<br>CAS No 401479-02-5 | 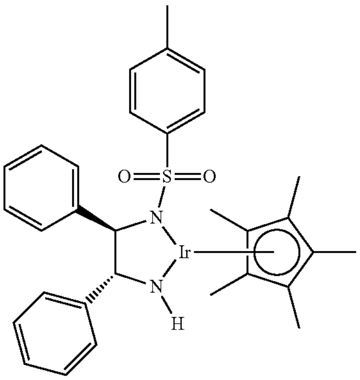 |
| 6052 | [Ir(cp*)((R,R,R)-Cs-DPEN-2H)]<br>CAS No 895579-52-9 | 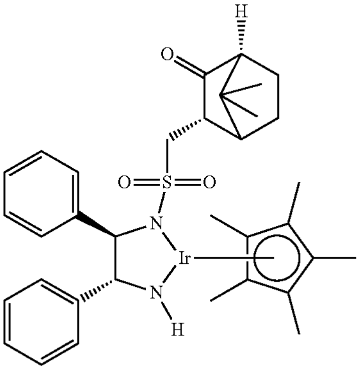 |
| 6053 | [Ir(cp*)((S,S)-TFMs-DPEN-2H)]<br>CAS No 1807637-08-6 | 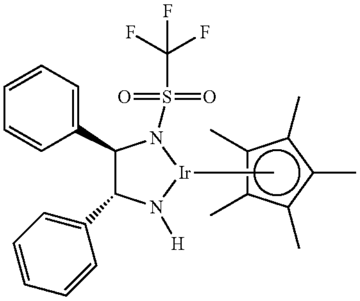 |
| 6054 | [Ir(cp*)((S,S)-TIPBs-DPEN-2H)]<br>CAS No. 1073339-77-1 | 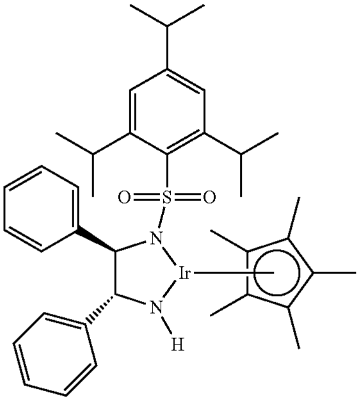 |

-continued

| (Pre-) Catalysts and Ligands | | |
|---|---|---|
| Number | Abbreviation | Structure |
| 6055 | [Ir(cp*)((S,S)-Ts-1,3,5-MeDPEN-2H)]<br>CAS No 2376389-13-6 | 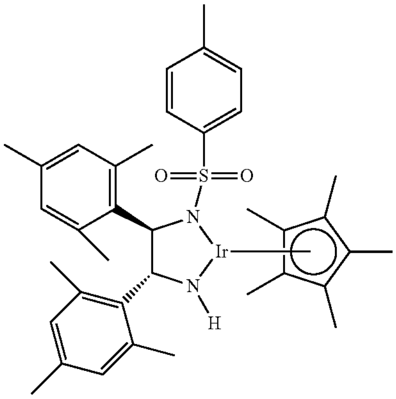 |
| 6056 | [Ir(cp*)((R,R)-Ts-DACH-2H)]<br>CAS No. 1099830-96-2 | 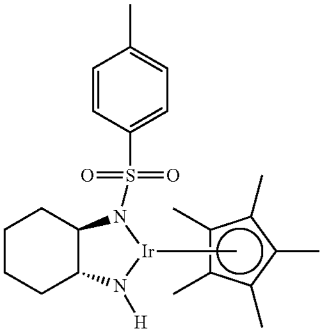 |
| 680 | [IrClH$_2$((S)-DTB-SpiroPAP-3-Me)]<br>CAS No 1418483-59-6<br>Available from Jiuzhou Pharma, CN<br>Catalogue No. JZ-S033-2 | 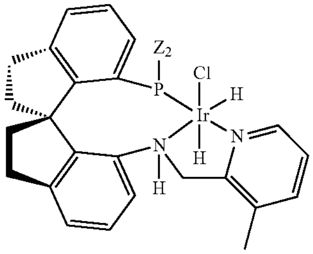<br>Z = 3,5-$^t$Bu$_2$—C$_6$H$_3$ |
| 682 | [IrClH$_2$((S)-DTB-SpiroSAP)]<br>CAS No not available<br>Available from Jiuzhou Pharma, CN<br>Catalogue No. JZ-S034-2 | 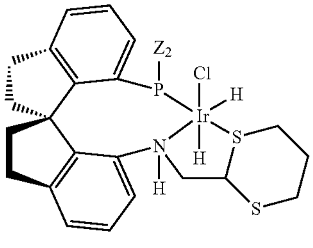<br>Z = 3,5-$^t$Bu$_2$—C$_6$H$_3$ |

-continued

| (Pre-) Catalysts and Ligands | | |
|---|---|---|
| Number | Abbreviation | Structure |
| 6046 | [IrClH$_2$((S,S,S)-DTB-PSpiroPAP-3-Me)]<br>CAS No not available<br>Available from Jiuzhou Pharma, CN<br>Catalogue No. JZ-S036-1 | 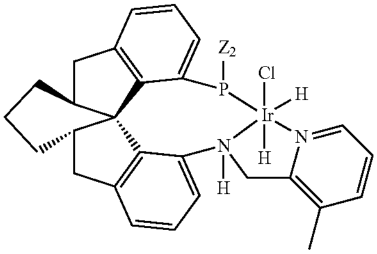<br>Z = 3,5-$^t$Bu$_2$—C$_6$H$_3$ |
| 6048 | [IrClH$_2$((S)-DTB-SpiroPAP)]<br>CAS No not available<br>Available from Jiuzhou Pharma, CN<br>Catalogue No. not available | 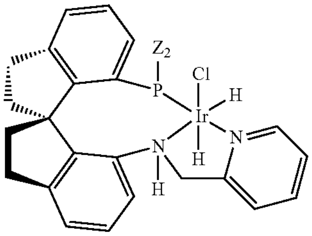<br>Z = 3,5-$^t$Bu$_2$—C$_6$H$_3$ |
| 6049 | [IrClH$_2$(R)-DTB-SpiroPAP-4-tBu)]<br>CAS No not available<br>Available from Jiuzhou Pharma, CN<br>Catalogue No. not available | 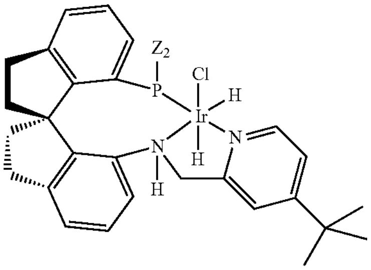<br>Z = 3,5-$^t$Bu$_2$—C$_6$H$_3$ |
| 6050 | [IrClH$_2$((R)-DTB-SpiroPAP-6-Me)]<br>CAS No not available<br>Available from Jiuzhou Pharma, CN<br>Catalogue No. not available | 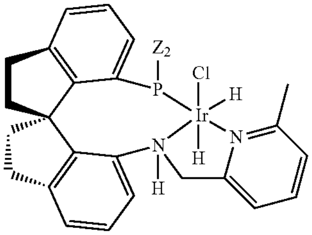<br>Z = 3,5-$^t$Bu$_2$—C$_6$H$_3$ |
| 1508 | (S)-DTB-SpiroPAP-3-Me<br>CAS No not available<br>Available from Jiuzhou Pharma, CN<br>Catalogue No. JZ-S022-2 | 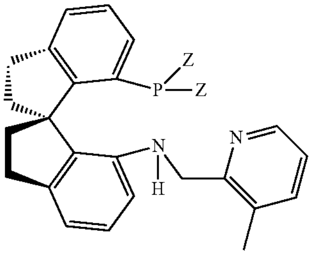<br>Z = 3,5-$^t$Bu$_2$—C$_6$H$_3$ |

-continued (Pre-) Catalysts and Ligands

| Number | Abbreviation | Structure |
|---|---|---|
| 600 | $[Ir(cod)_2]BF_4$<br>CAS No 35138-23-9 | 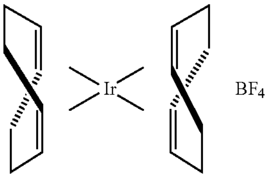 |
| 601 | $[IrCl(COD)]_2$<br>CAS No 12112-67-3 | 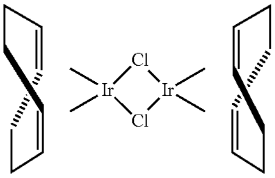 |
| 650 | [Ir(acac)(COD)]<br>CAS No 12154-84-6 | 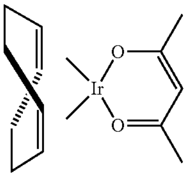 |
| 657 | $[Ir(OMe)(COD)]_2$<br>CAS No 12148-71-9 | 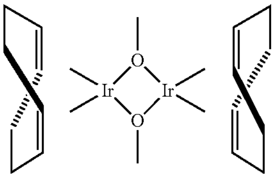 |

Analytical Methods a) Achiral LC Method to Determine the Conversion and Purifies of 1, 3 and the Cis- and Trans-Isomers of 4-6

| | |
|---|---|
| Stationary phase | Kinetex ® (2.6 μm PFP 100 Å, LC Column 50 × 4.6 mm) |
| Eluent: | A) Acetonitrile B) H2O + 5% Acetonitrile D) TBAHS Puffer (1 g TBAHS in 800 mL Acetonitrile und 200 mL H2O). Pump program (gradient): 10 A:80 B:10 D → 80 A:10 B:10 D |
| Run time: | 16 min |
| Flow: | 1 mL/min |
| Column oven temperature | 40° C. |
| Injection volume: | 5 uL |
| Detection: | DAD 210 nm |
| Retention Times: | 1, 13.23 min; 3, 6.91 min; trans-4, 6.04 min; cis-4, 5.73 min; trans-5, 5.49 min; cis-5, 5.19 min; trans-6 2.40 min; cis-6 2.18 min |

b) Chiral LC Method to Determine the Enantiomeric Purity of 3

| | |
|---|---|
| Stationary phase: | Daicel Chiralpak IC-3, L = 150 mm, ID = 4.6 mm, 3.0 μm |
| Eluent: | A) H2O + 5% Acetonitrile B) Acetonitrile C) 6.25-6.35 g ammonium formate in 950.0 mL Water adjusted to pH 9.0 with ammonium hydroxide solution (25%) + 50.0 mL acetonitrile pump program (isocratic): 60 A:30 B:10 C |
| Run time: | 20 min |
| Flow: | 1 mL/min |
| Column oven temperature: | 30° C. |
| Injection volume: | 2.5 uL |

-continued

| | |
|---|---|
| Detection: | DAD 254 nm |
| Retention Times: | (S)-3, 10.60 min; (R)-3, 12.20 min |

c) Chiral LC Method to Determine the Enantiomeric Purifies of 3, 4, 5 and 6

| | |
|---|---|
| Stationary phase: | Daicel Chiralpak IB-N; L = 150 mm, ID = 4.6 mm, 3.0 μm |
| Eluent: | A) CO2 B) Isopropanol, pump program (isocratic): 90 A:10 B |
| Run time: | 9 min |

-continued

| | |
|---|---|
| Flow: | 3 mL/min |
| Column oven temperature: | 20° C. |
| Injection volume: | 5 uL |
| Detection: | DAD 220 nm |
| Retention Times: | 1, 1.19 min; (R)-3, 1.85 min; (S)-3, 1.95 min; (R,R)-4, 2.24 min; (S,S)-4, 2.58 min; (R,S)-4, 3.09 min; (S,R)-4, 3.93 min; (R,R)-5, 3.08 min; (S,S)-5, 3.92 min; (R,S)-5, 2.33 min; (S,R)-5, 2.33 min; (R,R)-6, 5.11 min; (S,S)-6, 5.78 min; (R,S)-6, 6.37 min; (S,R)-6, 6.95 min |

1. Preparation of (R)-3 Via Asymmetric Hydrogenation of 1

Example 1.1

In a glove box under argon atmosphere, a 380 mL autoclave was charged with 1 (20.0 g, 78.5 mmol), 630 (60.2 mg, $78.3\times10^{-6}$ mol, S/C 1,000) and EtOH (200 mL). The autoclave was sealed and removed from the glove box, connected to a hydrogen line, pressurized with hydrogen gas to 70 bar and heated to 30° C. Under stirring, the hydrogenation was ran at a constant hydrogen pressure of 70 bar. Reaction samples were taken after 1 h (50% conversion) and 2 h (>99.9% conversion) to follow the progress of the reaction. After a total reaction time of 2.5 h, the autoclave was vented and allowed to cool to room temperature. The reaction mixture was transferred with aid of EtOH (20 mL) from the autoclave into a 500 mL round bottomed flask and the orange reaction solution rotatory evaporated at 40° C./10 mbar to constant weight to yield crude (R)-3 (19.9 g) with 96.7 area-% purity and 94.3% ee. 0.9% of trans-4 was detected as major impurity (note: trans-4 demonstrated to have limited stability and converted during handling and storage gradually into trans-5).

Next, crude (R)-3 (5.00 g) was dissolved in $iPr_2O$ (25 mL) at 60° C. The clear solution was allowed to cool to 0° C. within 6 h and stirred at this temperature for another 1.5 h. The formed white crystals were filtered, washed with 9 mL of ice cold $iPr_2O$ and dried for 1 h at 40° C. under vacuum (10 mbar) to afforded pure (R)-3 (4.15 g, 82% yield) with 99.9 area-% purity and 99.6% ee.

Analytical Data for 3

LC-MS ESI (m/z): 256.0 [M+]

$^1$H-NMR ($CDCl_3$, 600 MHz): δ ppm 7.89 (d, J=8.8 Hz, 2H), 7.41-7.50 (m, 3H), 4.65 (td, J=5.8, 3.8 Hz, 1H), 4.28 (q, J=7.2 Hz, 2H), 3.46-3.53 (m, 1H), 3.38-3.45 (m, 1H), 3.27 (d, J=5.6 Hz, 1H), 1.29 (t, J=7.1 Hz, 3H)

Analytical Data for Trans-4

GC-MS ESI (m/z): 258.0 [M+]

1H NMR (DMSO-D6, 600 MHz): δ ppm 7.35-7.38 (m, 2H), 7.32-7.35 (m, 2H), 5.44 (br s, 2H), 4.73 (br d, J=9.6 Hz, 1H), 4.25 (br d, J=8.6 Hz, 1H), 4.06 (q, J=7.1 Hz, 2H), 1.53-1.78 (m, 1H), 1.45-1.99 (m, 1H), 1.17 (t, J=7.1 Hz, 3H)

Example 1.2

In a glove box under argon atmosphere, a 380 mL autoclave was charged with 1 (20.0 g, 78.5 mmol), 629 (48.4 mg, $78.3\times10^{-6}$ mol, S/C 1,000) and EtOH (200 mL). The autoclave was sealed and removed from the glove box, connected to a hydrogen line, pressurized with hydrogen gas to 70 bar and heated to 30° C. Under stirring, the hydrogenation was ran at a constant hydrogen pressure of 70 bar. A reaction sample was taken after 3.5 h (98% conversion) to follow the progress of the reaction. After a total reaction time of 4 h, the autoclave was vented and allowed to cool to room temperature. The reaction mixture was transferred with aid of EtOH (20 mL) from the autoclave into a 500 mL round bottomed flask and the orange reaction solution rotatory evaporated at 40° C./10 mbar to constant weight to yield crude (R)-3 (20.0 g) with 94 area-% purity and 94.5% ee. 1.3% of trans-4 was detected as major impurity. Next, crude (R)-3 (20.0 g) was dissolved in $iPr_2O$ (200 mL) at 40° C. The clear solution was then allowed to cool to 0° C. within 6 h and stirred at this temperature for another 1.5 h. The formed white crystals were filtered, washed with 45 mL of ice cold $iPr_2O$ and dried for 1 h at 40° C. under vacuum (10 mbar) to afforded 15.62 g of pure (R)-3 (15.62 g, 78% yield) with 99.2 area-% purity and 99.8% ee.

Examples 1.3-1.6

In analogy to Example 1.1, 1 (0.5 g, 1.96 mmol) was hydrogenated for 20 h in EtOH (5 mL) and the presence of the catalysts as listed in Table 1 at 30° C. and an initial hydrogen pressure of 70 bar $H_2$.

TABLE 1

| exp | catalyst | conv [%] | 3 [area-%] | (R)-3 [% ee] | trans-4 [area-%] |
|---|---|---|---|---|---|
| 1.3 | 629 | >99.9 | 90 | 95.0 | 7 |
| 1.4 | 6051 | >99.9 | 95.8 | 95.0 | 2.2 |
| 1.5 | 6052 | >99.9 | 94 | 92 | 1.9 |
| 1.6 | 6053 | 60 | 40 | 63 (S) | 0 |

Examples 1.7-1.10

In analogy to Example 1.1, 1 (0.25 g, 0.98 mmol) was hydrogenated for 2 h in EtOH (5 mL) and the presence of the catalysts as listed in Table 2 at 30° C. and an initial hydrogen pressure of 70 bar $H_2$.

TABLE 2

| exp | catalyst | conv [%] | 3 [area-%] | (R)-3 [% ee] | trans-4 [area-%] |
|---|---|---|---|---|---|
| 1.7 | 629 | 59 | 52 | 95.0 | 0 |
| 1.8 | 6054 | 21 | 9 | n.d. | 0 |
| 1.9 | 6055 | 9 | 7 | n.d. | 0 |
| 1.10 | 6056 | 42 | 38 | 15 | 0 |

Examples 1.11-1.14

In analogy to Example 1.1, 1 (0.25 g, 0.98 mmol) was hydrogenated for 2 h in EtOH (5 mL) at 30° C. in the presence of the catalysts (S/C 1,000) and initial hydrogen pressures as listed in Table 3.

TABLE 3

| exp | catalyst | p [bar] | conv 1%] | 3 [area-%] | (R)-3 [% ee] | trans-4 [area-%] |
|---|---|---|---|---|---|---|
| 1.11 | 629 | 30 | 75 | 71 | n.d. | 0 |
| 1.12 | 629 | 50 | 89 | 87 | n.d. | 0 |
| 1.13 | 630 | 30 | >99.9 | 96.5 | 95.7 | 0 |
| 1.14 | 630 | 50 | >99.9 | 95.9 | 95.7 | 0.4 |

Examples 1.15-1.20

In analogy to Example 1.1, 1 (0.25 g, 0.98 mmol) was hydrogenated for 2 h in EtOH (5 mL) at 30° C. and an initial hydrogen pressures of 70 bar in the presence of various amounts of catalysts and DBU as base as listed in Table 4.

TABLE 4

| exp | catalyst | S/C | DBU [eq] | conv [%] | 3 [area-%] | (R)-3 [% ee] | trans-4 [area-%] |
|---|---|---|---|---|---|---|---|
| 1.15 | 630 | 1'000 | — | >99.9 | 96.3 | 95.6 | 0.3 |
| 1.16 | 630 | 1'000 | 10 | 95.0 | 94.5 | 96.5 | 0 |
| 1.17 | 630 | 500 | 50 | >99.9 | 97 | n.d. | 1.4 |
| 1.18 | 630 | 1000 | 50 | 98.3 | 96.9 | 96.4 | 0 |
| 1.19 | 630 | 2'000 | 50 | 56 | 55 | n.d. | 0 |
| 1.20 | 630 | 2'000 | — | 46 | 46 | n. d. | 0 |

2. Preparation of (R,R)-6 Via Asymmetric Hydrogenation of 1

Examples 2.1

In a glove box under argon atmosphere, a 380 mL autoclave was charged with 1 (10.0 g, 39.3 mmol), 680 (38.4 mg, $39.3\times10^{-6}$ mol, S/C 1,000), DBU (597.8 mg, 3.93 mmol, S/B 10) and EtOH (200 mL). The autoclave was sealed and removed from the glove box, connected to a hydrogen line and pressurized with hydrogen gas to 70 bar and heated to 30° C. Under stirring, the hydrogenation was run at a constant hydrogen pressure of 70 bar. After a total reaction time of 20 h (>99.9% conversion), the autoclave was vented and allowed to cool to room temperature. The reaction mixture was transferred with aid of EtOH (20 mL) from the autoclave into a 500 mL round bottomed flask and the orange reaction solution rotatory evaporated at 40° C./10 mbar to constant weight to yield crude 6 (9.0 g) with 98.4 area-% purity (DBU not integrated) and a trans cis ratio of 7.7. (R,R)-6 was obtained with 98.8% ee.

Analytical Data for Cis-5

GC-MS ESI (m/z): 212.0 [M+]

$^1$H-NMR (DMSO-D6, 600 MHz): δ 7.47-7.51 (m, 2H), 7.42 (d, J=8.3 Hz, 2H), 6.02 (br s, 1H), 5.40 (dd, J=10.8, 5.4 Hz, 1H), 4.62 (dd, J=10.7, 8.6 Hz, 1H), 2.89 (ddd, J=12.2, 8.2, 5.4 Hz, 1H), 1.93 (dt, J=12.1, 11.0 Hz, 1H)

Analytical Data for Trans-5

GC-MS ESI (m/z): 212.0 [M+]

1H-NMR (DMSO-D6, 600 MHz): δ 7.47 (d, J=8.7 Hz, 2H), 7.40-7.42 (m, 2H), 6.18 (br d, J=5.2 Hz, 1H), 5.68 (t, J=6.7 Hz, 1H), 4.38 (dt, J=7.0, 4.9 Hz, 1H), 2.44-2.48 (m, 1H), 2.36-2.42 (m, 1H)

Analytical Data for Trans-6

GC-MS ESI (m/z): 216.0 [M+]

$^1$H NMR (400 MHz, DMSO) δ 7.40-7.31 (m, 4H), 5.23 (d, J=4.9 Hz, 1H), 4.75 (dd, J=9.9, 4.8 Hz, 1H), 4.50 (dd, J=6.5, 5.5 Hz, 2H), 3.68-3.67 (m, 1H), 3.30-3.24 (m, 2H), 1.67-1.61 (m, 1H), 1.44-1.39 (m, 1H).

$^{13}$C NMR (101 MHz, DMSO) δ 146.6, 131.3, 128.4, 127.9, 68.7, 68.6, 66.8, 44.3.

Analytical Data for Cis-6

GC-MS ESI (m/z): 216.0 [M+]

$^1$H-NMR ($CDCl_3$, 600 MHz): δ ppm 7.31-7.34 (m, 2H), 7.32 (s, 2H), 4.98 (dd, J=9.9, 2.5 Hz, 1H), 4.04 (br d, J=2.4 Hz, 1H), 3.45-3.70 (m, 2H), 2.76 (s, 1H), 1.65-1.95 (m, 2H), 1.08 (s, 2H).

$^{13}$C-NMR ($CDCl_3$, 151 MHz) δ 142.7, 133.3, 128.7, 127.1, 73.82, 72.3, 66.7, 41.6.

Examples 2.2

In a glove box under argon atmosphere, a 380 mL autoclave was charged with 1 (10.0 g, 39.3 mmol), 601 (29.4 mg, $19.6\times10^{-6}$ mol, S/Ir 1,000), 1508 (13.2 mg, $39.3\times10^{-6}$ mol, S/L 1,000), DBU (597.8 mg, 3.93 mmol, S/B 10) and EtOH (200 mL). The autoclave was sealed and removed from the glove box, connected to a hydrogen line and pressurized with hydrogen gas to 70 bar and heated to 30° C. Under stirring, the hydrogenation was ran at a constant hydrogen pressure of 70 bar. After a total reaction time of 20 h (>99.9% conversion), the autoclave was vented and allowed to cool to room temperature. The reaction mixture was transferred with aid of EtOH (20 mL) from the autoclave into a 500 mL round bottomed flask and the orange reaction solution rotatory evaporated at 40° C./10 mbar to constant weight to yield crude 6 (9.1 g) with 96.5 area-% purity (DBU not integrated) and a trans/cis ratio of 8.3. (R,R)-6 was obtained with >99.9% ee.

Specified Impurity: Trans-5 (0.8%)

Examples 2.3

In a glove box under argon atmosphere, a 380 mL autoclave was charged with 1 (10.0 g, 39.3 mmol), 601, 29.4 mg, $19.6\times10^{-6}$ mol, S/Ir 1,000), 1508 (13.2 mg, $39.3\times10^{-6}$ mol, S/L 1,000), KOtBu (437.6 mg, 3.93 mmol, S/B 10) and EtOH (200 mL). The autoclave was sealed and removed from the glove box, connected to a hydrogen line and pressurized with hydrogen gas to 70 bar and heated to 30° C. Under stirring, the hydrogenation was ran at a constant hydrogen pressure of 70 bar. After a total reaction time of 42 h (>99.9% conversion), the autoclave was vented and allowed to cool to room temperature. The reaction mixture was transferred with aid of EtOH (20 mL) from the autoclave into a 500 mL round bottomed flask and the orange reaction solution rotatory evaporated at 40° C./10 mbar to constant weight to yield crude 6 (9.0 g) with 84.2 area-% purity and a trans/cis ratio of 8.0. (R,R)-6 was obtained with 98.6% ee.

Specified Impurity: Trans-5 (0.9%)

Examples 2.4-2.8

In analogy to Example 2.1, 1 (0.25 g, 0.98 mmol) was hydrogenated for 20 h in EtOH (5 mL) at 30° C. and an initial hydrogen pressure of 70 bar in the presence KOtBu ($4.9\times10^{-5}$ mol, S/B 20) and of the catalysts (S/C 1,000) as listed in Table 5.

TABLE 5

| exp | cat | conv [%] | 3 [area-%] | trans-4 [area-%] | trans-5 [area-%] | 6 [area-%] | (R,R)-6 [% ee] | 6 trans/cis] |
|---|---|---|---|---|---|---|---|---|
| 2.4 | 682 | >99.9 | 0 | 51 | 27 | 15 | 99.9 | 35 |
| 2.5 | 6046 | 85 | 67 | 0 | 0 | 0 | — | — |
| 2.6 | 6048 | >99.9 | 0.3 | 0 | 1.2 | 93 | 99.9 | 7.8 |
| 2.7 | 6049 | 99.1 | 1.1 | 0 | 1.4 | 88 | 99.8 | 7.2 |
| 2.8 | 6050 | 77 | 56 | 0.4 | 0 | 0 | — | — |

Examples 2.9-2.16

In analogy to Example 2.2, 1 (0.25 g, 0.98 mmol) was hydrogenated for 20 h in EtOH (5 mL) at 30° C. and an initial hydrogen pressure of 70 bar in the presence of 1508 ($0.98\times10^{-6}$ mol, S/L 1,000), the presence or absence of DBU ($0.98\times10^{-4}$ mol, S/B 10) and the presence of a pre-catalyst (S/Ir 1,000) as listed in Table 6.

TABLE 6

| exp | pre-catalyst | base | conv [%] | 3 [area-% | trans-4 [area-%] | trans-5 [area-%] | 6 [area-%] | (R,R)-6 [% ee] | 6 [trans/cis] |
|---|---|---|---|---|---|---|---|---|---|
| 2.9 | 600 | DBU | 99.5 | 0 | 1.0 | 1.5 | 93 | 99.9 | 8.3 |
| 2.10 | 601 | DBU | 99.6 | 0 | 0 | 0.7 | 96.7 | 99.6 | 7.5 |
| 2.11 | 650 | DBU | 99.7 | 0 | 0 | 0.8 | 96.0 | 99.6 | 7.3 |
| 2.12 | 657 | DBU | 99.3 | 0 | 0 | 0.7 | 97.3 | 99.5 | 6.9 |
| 2.13 | 600 | — | 82 | 69 | 1.0 | 0 | 0 | — | — |
| 2.14 | 601 | — | 95 | 52 | 7 | 1.7 | 0 | — | — |
| 2.15 | 650 | — | 75 | 64 | 0.6 | 0 | 0 | — | — |
| 2.16 | 657 | — | >99.9 | 20 | 70 | 0.5 | 0 | — | — |

Examples 2.17-2.29

In analogy to Example 2.1, 1 (0.10 g, 0.39 mmol or 0.25 g, 0.98 mmol) was hydrogenated for 20 h in EtOH (2 mL for 0.10 g scale experiments, resp. 4 mL for 0.25 g experiments) at 30° C. and an initial hydrogen pressure of 70 bar in the presence of 680 ($9.8 \times 10^{-7}$ mol, S/C 1,000), the presence of a base (S/B 10) as listed in Table 7.

TABLE 7

| exp | base | conv [%] | 3 [area-% | trans-4 [area-%] | trans-5 [area-%] | 6 [area-%] | (R,R)-6 [% ee] | 6 [trans/cis] |
|---|---|---|---|---|---|---|---|---|
| 2.17 | — | 8 | 6 | 0 | 0 | 0 | — | — |
| 2.18 | KOtBu | >99.9 | 0 | 1.6 | 0 | 85 | 99.9 | 13 |
| 2.19 | $NaHCO_3$ | 79 | 67 | 2.4 | 0 | 0 | — | — |
| 2.20 | DBU | >99.9 | 0 | 3.5 | 0 | 91 | 99.9 | 20 |
| 2.21 | $NEt_3$ | >99.9 | 0 | 62 | 34 | 0.7 | — | — |
| 2.22 | $KH_2PO_4$ | 25 | 20 | 0 | 0 | 0 | — | — |
| 2.23 | $Cs_2CO_3$ | 96.7 | 0 | 0 | 0 | 85 | 99.6 | 12 |
| 2.24 | NaOCHO | 51 | 40 | 0 | 0 | 0 | — | — |
| 2.25 | NaOAc | 57 | 46 | 0 | 0 | 0 | — | — |
| 2.26 | DABCO | 93 | 86 | 3.4 | 0 | 0 | — | — |
| 2.27 | DBN | >99.9 | 0 | 26 | 50 | 17 | n.d. | 38 |
| 2.28 | BIPY | 6 | 11 | 0 | 0 | 0 | — | — |
| 2.29 | MTBD | >99.9 | 0 | 0 | 0.6 | 96.3 | 99.9 | 8.3 |

Examples 2.30-2.42

In analogy to Example 2.1, 1 (0.25 g, 0.98 mmol) was hydrogenated for 20 h at 30° C. and an initial hydrogen pressure of 70 bar in the presence of 680 (either $0.98 \times 10^{-6}$ mol, S/C 1,000 or $0.20 \times 10^{-6}$ mol, S/C 5,000), the presence of KOtBu (0.98 mmol, S/B 10) and a solvent or solvent mixtures (5 mL) as listed in Table 8.

TABLE 8

| exp | solvent | S/C | conv [%] | 3 [area-%] | trans-4 [area-%] | trans-5 [area-%] | 6 [area-%] | (R,R)-6 [% ee] | 6 [trans/cis] |
|---|---|---|---|---|---|---|---|---|---|
| 2.30 | EtOH | 1'000 | >99.9 | 0 | 1.6 | 0 | 85 | 99.8 | 13 |
| 2.31 | MeOH | 1'000 | >99.9 | 0 | 0 | 0 | 92 | 97.0 | 4.0 |
| 2.32 | EtOH | 5'000 | 53 | 14 | 0 | 0 | 0 | — | — |
| 2.33 | MeOH | 5'000 | 68 | 20 | 5 | 0 | 0 | — | — |
| 2.34 | iPrOH | 5'000 | 23 | 5 | 0 | 0 | 0 | — | — |
| 2.35 | tAmOH | 5'000 | 15 | 2.0 | 0 | 0 | 0 | — | — |
| 2.36 | DCM | 5'000 | 22 | 6 | 0 | 0 | 0 | — | — |
| 2.37 | THF | 5'000 | 19 | 8 | 0 | 0 | 0 | — | — |
| 2.38 | toluene | 5'000 | 16 | 4.4 | 0 | 0 | 0 | — | — |
| 2.39 | TFE | 5'000 | 52 | 16 | 2.9 | 0 | 0 | — | — |
| 2.40 | dioxane | 5'000 | 3.8 | 0 | 0 | 0 | 0 | — | — |
| 2.41 | EtOH/ $H_2O$ 95:5 | 5'000 | 99.0 | 47 | 0 | 0 | 0 | — | — |
| 2.42 | EtOH/ dioxane 1:1 | 5'000 | 28 | 6 | 0 | 0 | 0 | — | — |

Examples 2.43-2.51

In analogy to Example 2.1, 1 (0.20 g, 0.79 mmol) was hydrogenated for 20 h in EtOH (5 mL) the presence of 680 (either $0.79\times10^{-6}$ mol, S/C 9,000 or $0.16\times10^{-6}$ mol S/C 5,000), the presence of various amounts of KOtBu, different temperatures and initial hydrogen pressures all as listed in Table 9.

TABLE 9

| exp | S/C | S/B | T | p [bar] | conv [%] | 3 [area-%] | trans-4 [area-%] | trans-5 [area-%] | 6 [area-%] | (R,R)-6 [% ee] | 6 [trans/cis] |
|---|---|---|---|---|---|---|---|---|---|---|---|
| 2.43 | 1000 | 1000 | 30 | 70 | 30 | 25 | 0 | 0 | 0 | — | — |
| 2.44 | 1000 | 100 | 30 | 70 | 75 | 65 | 0 | 0 | 0 | — | — |
| 2.45 | 1000 | 10 | 30 | 70 | >99.9 | 0 | 0 | 0 | 87 | 98.8 | 7.3 |
| 2.46 | 1000 | 1000 | 60 | 70 | 85 | 76 | 0 | 0 | 0 | — | — |
| 2.47 | 1000 | 100 | 60 | 70 | >99.9 | 0 | 0 | 0 | 88 | 97.9 | 7.3 |
| 2.48 | 1000 | 10 | 60 | 70 | >99.9 | 0 | 0 | 0 | 8 | 96.5 | 5.2 |
| 2.49 | 5000 | 1 | 30 | 70 | 17 | 0 | 1.2 | 0 | 13 | 99.9 | 7.8 |
| 2.50 | 5000 | 1 | 30 | 100 | 16 | 0 | 1.3 | 0 | 12 | 99.9 | 8.0 |
| 2.51 | 5000 | 1 | 90 | 100 | >99.9 | 0 | 4.6 | 0 | 0 | — | — |

Example 2.52

In a glove box under argon atmosphere, a 180 mL autoclave was charged with 1 (1.00 g, 3.93 mmol), 629 (1.21 mg, $1.96\times10^{-6}$ mol, S/C 2,000), 680 (1.92 mg, $1.96\times10^{-6}$ mol, S/C 2,000), DBU (59.8 mg, $3.93\times10^{-4}$ mol, S/B 10) and EtOH (20 mL). The autoclave was sealed and removed from the glove box, connected to a hydrogen line and pressurized with hydrogen gas to 70 bar and heated to 30° C. Under stirring, the hydrogenation was ran at a constant hydrogen pressure of 70 bar. Reaction samples were taken at different time points (see Table 10) to follow the progress of the reaction.

TABLE 10

| ret [h] | conv [%] | 3 [area-%] | trans-4 [area-%] | trans-5 [area-%] | 6 [area-%] | (R,R)-6 [% ee] | 6 [trans/cis] |
|---|---|---|---|---|---|---|---|
| 1 | 16 | 11 | 0 | 0 | 0 | — | — |
| 2 | 51 | 46 | 0.1 | 0 | 0.2 | — | — |
| 4 | 96.4 | 76 | 11 | 7 | 0.3 | — | — |
| 6 | 95.9 | 0.7 | 30 | 41 | 17 | 99.9 | 48 |
| 8 | 97.5 | 0 | 2.0 | 14 | 74 | 99.9 | 55 |
| 24 | >99.9 | 0 | 0 | 0.8 | 98.4 | 99.9 | 14 |

Example 2.53

In a glove box under argon atmosphere, a 180 mL autoclave was charged with 1 (1.00 g, 3.93 mmol), 629 (2.42 mg, $3.93\times10^{-6}$ mol, S/C 1,000), 680 (0.77 mg, $0.79\times10^{-6}$ mol, S/C 5,000), DBU (30.0 mg, $1.97\times10^{-4}$ mol, S/B 20) and EtOH (20 mL). The autoclave was sealed and removed from the glove box, connected to a hydrogen line and pressurized with hydrogen gas to 70 bar and heated to 30° C. Under stirring, the hydrogenation was ran at a constant hydrogen pressure of 70 bar. Reaction samples were taken at different time points (see Table 11) to follow the progress of the reaction.

TABLE 11

| ret [h] | conv [%] | 3 [area-%] | trans-4 [area-%] | trans-5 [area-%] | 6 [area-%] | (R,R)-6 [% ee] | 6 [trans/cis] |
|---|---|---|---|---|---|---|---|
| 1 | 52 | 50 | 0 | 0 | 0 | — | — |
| 2 | 84 | 82 | 0.3 | 0 | 0 | — | — |
| 4 | 99.1 | 76 | 16 | 6 | 0 | — | — |
| 6 | 98.5 | 23 | 46 | 24 | 1.2 | — | — |
| 8 | 97.7 | 3.8 | 49 | 28 | 13 | n.d. | n.d. |
| 22 | >99.9 | 0 | 0.9 | 2.7 | 94 | 99.9 | 32 |

Example 2.54

In a glove box under argon atmosphere, a 180 mL autoclave was charged with 1 (1.00 g, 3.93 mmol), 629 (2.42 mg, $3.93\times10^{-6}$ mol, S/C 1,000), 680 (0.77 mg, $0.79\times10^{-6}$ mol, S/C 5,000), DBU (5.98 mg, $3.93\times10^{-5}$ mol, S/B 100) and EtOH (20 mL). The autoclave was sealed and removed from the glove box, connected to a hydrogen line and pressurized with hydrogen gas to 70 bar and heated to 30° C. Under stirring, the hydrogenation was ran at a constant hydrogen pressure of 70 bar. Reaction samples were taken at different time points (see Table 12) to follow the progress of the reaction.

TABLE 12

| ret [h] | conv [%] | 3 [area-%] | trans-4 [area-%] | trans-5 [area-%] | 6 [area-%] | (R,R)-6 [% ee] | 6 [trans/cis] |
|---|---|---|---|---|---|---|---|
| 1 | 15 | 13 | 0 | 0 | 0 | — | — |
| 2 | 49 | 47 | 0 | 0 | 0 | — | — |
| 4 | 83 | 76 | 1.1 | 0 | 0 | — | — |
| 6 | 98.3 | 81 | 9 | 1.6 | 0.4 | — | — |
| 8 | 98.9 | 2.3 | 28 | 14 | 53 | 99.9 | 55 |
| 22 | >99.9 | 0 | 0 | 0 | 98.0 | 99.9 | 16 |

Example 2.55

In a glove box under argon atmosphere, a 180 mL autoclave was charged with 1 (1.00 g, 3.93 mmol), 630 (3.00 mg, $3.93\times10^{-6}$ mol, S/C 1,000) and EtOH (20 mL). The autoclave was sealed and removed from the glove box, connected to a hydrogen line and pressurized with hydrogen gas to 30 bar and heated to 30° C. Under stirring, the hydrogenation was ran at a constant hydrogen pressure of 30 bar for 4 h. Afterward the pressure was released to 1-2 bar and the autoclave returned to the glove box where under argon atmosphere it was opened and charged with 680 (0.77 mg, $0.79\times10^{-6}$ mol, S/C 5,000), DBU (30.0 mg, $1.97\times10^{-4}$ mol, S/B 20). The autoclave was sealed again and removed from the glove box, connected to a hydrogen line and pressurized with hydrogen gas to 70 bar and heated to 30° C. Under stirring, the hydrogenation was ran at a constant hydrogen pressure of 70 bar. The reaction was continued for 18 h at to 70 bar and heated to 30° C. Reaction samples were taken at different time points (see Table 13) to follow the progress of the reaction.

TABLE 13

| | | 3 | | trans-4 | trans-5 | 6 | (R,R)-6 | 6 |
|---|---|---|---|---|---|---|---|---|
| ret [h] | conv [%] | [area-%] | [% ee] | [area-%] | [area-%] | [area-%] | [% ee] | [trans/cis] |
| 1 | 54 | 52 | — | 0 | 0 | 0 | — | — |
| 2 | 87 | 85 | 95 | 0 | 0 | 0 | — | — |
| 4 | >99.9 | 93 | 95.2 | 0.4 | 0 | 0 | — | — |
| 6 | >99.9 | 31 | — | 19 | 18 | 0.7 | — | — |
| 23 | >99.9 | 0.8 | — | 23 | 10 | 56 | 99.9 | 78 |

Example 2.56

In a glove box under argon atmosphere, a 180 mL autoclave was charged with 1 (1.00 g, 3.93 mmol), 630 (3.00 mg, $3.93\times10^{-6}$ mol, S/C 1,000), 680 (0.77 mg, $0.79\times10^{-6}$ mol, S/C 5,000), DBU (12.0 mg, $7.86\times10^{-5}$ mmol, S/B 50) and EtOH (20 mL). The autoclave was sealed and removed from the glove box, connected to a hydrogen line and pressurized with hydrogen gas to 30 bar and heated to 30° C. Under stirring, the hydrogenation was ran at a constant hydrogen pressure of 30 bar for 4 h. Afterward the pressure was increased to 70 bar and the reaction carried out for additional 19 h. Reaction samples were taken at different time points (see Table 14) to follow the progress of the reaction.

TABLE 14

| | | 3 | | trans-4 | trans-5 | 6 | (R,R)-6 | 6 |
|---|---|---|---|---|---|---|---|---|
| ret [h] | conv [%] | [area-%] | [% ee] | [area-%] | [area-%] | [area-%] | [% ee] | [trans/cis] |
| 1 | 34 | 34 | — | — | — | — | — | — |
| 2 | 48 | 48 | 92.4 | — | — | — | — | — |
| 4 | 67 | 66 | 91.9 | 0.2 | — | — | — | — |
| 6 | 74 | 73 | 91.1 | 0.3 | — | — | — | — |
| 23 | >99.9 | 0.9 | — | 3.8 | 0.3 | 92 | >99.9 | 20 |

Example 2.57

In a glove box under argon atmosphere, a 180 mL autoclave was charged with 1 (1.00 g, 3.93 mmol), 630 (3.00 mg, $3.93\times10^{-6}$ mol, S/C 1,000), 680 (0.77 mg, $0.79\times10^{-6}$ mol, S/C 5,000), DBU (12.0 mg, $7.86\times10^{-5}$ mmol, S/B 50) and EtOH (20 mL). The autoclave was sealed and removed from the glove box, connected to a hydrogen line and pressurized with hydrogen gas to 70 bar and heated to 30° C. Under stirring, the hydrogenation was ran at a constant hydrogen pressure of 70 bar for 23 h. Reaction samples were taken at different time points (see Table 15) to follow the progress of the reaction.

TABLE 15

| | | 3 | | trans-4 | trans-5 | 6 | (R,R)-6 | 6 |
|---|---|---|---|---|---|---|---|---|
| ret [h] | conv [%] | [area-%] | [% ee] | [area-%] | [area-%] | [area-%] | [% ee] | [trans/cis] |
| 1 | 30 | 30 | — | — | — | — | — | — |
| 2 | 62 | 61 | 92.6 | — | — | — | — | — |
| 4 | 96.0 | 91 | 92.7 | 3.9 | — | — | — | — |
| 6 | >99.9 | 43 | — | 40 | 16 | 0.4 | — | — |
| 23 | >99.9 | — | — | — | — | 98.1 | >99.9 | 15 |

Example 2.58

In a glove box under argon atmosphere, a 180 mL autoclave was charged with 1 (1.00 g, 3.93 mmol), 630 (3.00 mg, $3.93\times10^{-6}$ mol, S/C 1,000), 680 (0.77 mg, $0.79\times10^{-6}$ mol, S/C 5,000), DBU (30.0 mg, $1.97\times10^{-4}$ mol, S/B 20) and EtOH (20 mL). The autoclave was sealed and removed from the glove box, connected to a hydrogen line and pressurized with hydrogen gas to 70 bar and heated to 30° C. Under stirring, the hydrogenation was ran at a constant hydrogen pressure of 70 bar for 23 h. Reaction samples were taken at different time points (see Table 16) to follow the progress of the reaction.

TABLE 16

| | | 3 | | trans-4 | trans-5 | 6 | (R,R)-6 | 6 |
|---|---|---|---|---|---|---|---|---|
| ret [h] | conv [%] | [area-%] | [% ee] | [area-%] | [area-%] | [area-%] | [% ee] | [trans/cis] |
| 1 | 22 | 19 | — | — | — | — | — | — |
| 2 | 88 | 85 | 94.3 | 1.6 | — | — | — | — |
| 4 | 97 | 77 | 93.6 | 11 | 4.2 | — | — | — |
| 6 | >99.9 | 9 | — | 54 | 30 | 5 | — | — |
| 23 | >99.9 | — | — | 1.7 | 0.4 | 96.2 | >99.9 | 24 |

Example 2.59

In a glove box under argon atmosphere, a 380 mL autoclave was charged with 1 (15.0 g, 59 mmol), 630 (45.1 mg, $5.9\times10^{-5}$ mol, S/C 1,000), 680 (11.5 mg, $1.2\times10^{-5}$ mol, S/C 5,000), DBU (179.3 mg, 1.2 mmol, S/B 50) and EtOH (300 mL). The autoclave was sealed and removed from the glove box, connected to a hydrogen line and pressurized with hydrogen gas to 70 bar and heated to 30° C. Under stirring, the hydrogenation was ran at a constant hydrogen pressure of 70 bar. Reaction samples were taken at different time points (see Table 17) to follow the progress of the reaction. After a total reaction time of 48 h (>99.9% conversion), the autoclave was vented and allowed to cool to room temperature. The reaction mixture was transferred with aid of EtOH (200 mL) from the autoclave into a 500 mL round bottomed flask and the orange reaction solution rotatory evaporated at 40° C./10 mbar to constant weight to afford crude 6 (12.1 g—a higher yield would be achievable when omitting IPC sampling) with 99.4 area-% purity and a trans cis ratio of 15. (R,R)-6 was obtained with >99.9% ee.

Specified Impurities: Cis-6 (6.1%), Trans-4 (0.2%), Trans-5 (0.1%)

Next, crude (R,R)-6 (12.1 g) was suspended in iPrOAc (100 mL) and the slurry stirred for 2 h at 50° C. The suspension was cooled to 0° C. and stirred at this temperature for 1 h, filtered and the filter cake washed with ice-cold iPrOAc (60 ml) in 3 portions to afford after drying (25° C., 10 mbar) pure 6 (9.8 g, 77% yield) with 99.5 area-% purity and a trans cis ratio of 104. (R,R)-6 was obtained with >99.9% ee.

Specified Impurity: Cis-6 (0.95%)

Subsequently, (R,R)-6 (9.8 g) from above was dissolved in iPrOAc (78 ml) at 90° C. The colorless solution was cooled to 25° C. within 2 h whereby the product started to crystallize. The formed suspension was kept at 25° C. for 2 h and cooled to 0° C. within 30 min. The crystals were filtered and washed with ice-cold iPrOAc (30 ml) in 2 portions to afford after drying (25° C., 10 mbar) off-white, crystalline 6 (9.0 g, 71% yield—a higher yield would be achievable when omitting IPC sampling during the hydrogenation run) with >99.9 area-% purity and a trans cis ratio of 713. (R,R)-6 was obtained with >99.9% ee.

Specified Impurity: Cis-6 (0.14%)

TABLE 17

| | | 3 | | trans-4 | trans-5 | 6 | (R,R)-6 | 6 |
|---|---|---|---|---|---|---|---|---|
| ret [h] | conv [%] | [area-%] | [% ee] | [area-%] | [area-%] | [area-%] | [% ee] | [trans/cis] |
| 2 | 89 | 88 | 94 | 0.4 | 0 | 0 | — | — |
| 4 | >99.9 | 85 | 93 | 11 | 0 | 0.1 | — | — |
| 6 | >99.9 | 34 | 92 | 44 | 19 | 0.4 | — | — |
| 20 | >99.9 | 0 | — | 0.9 | 0.2 | 96.4 | >99.9 | 18 |
| 23 | >99.9 | 0 | — | 0.7 | 0.1 | 97.0 | >99.9 | 18 |
| 46 | >99.9 | 0 | — | 0.2 | 0.1 | 96.8 | >99.9 | 15 |

Example 2.60

In a glove box under argon atmosphere, a 380 mL autoclave was charged with 1 (15.0 g, 59 mmol), 630 (45.1 mg, $5.9\times10^{-5}$ mol, S/C 1,000), 680 (11.5 mg, $1.2\times10^{-5}$ mol, S/C 5,000), DBU (179.3 mg, 1.2 mmol, S/B 50) and EtOH (300 mL). The autoclave was sealed and removed from the glove box, connected to a hydrogen line and pressurized with hydrogen gas to 70 bar and heated to 30° C. Under stirring, the hydrogenation was ran at a constant hydrogen pressure of 70 bar. Reaction samples were taken at different time points (see Table 18) to follow the progress of the reaction. After a total reaction time of 23 h (>99.9% conversion), the autoclave was vented and allowed to cool to room temperature. The reaction mixture was transferred with aid of EtOH (200 mL) from the autoclave into a 500 mL round bottomed flask and the orange reaction solution rotatory evaporated at 40° C./10 mbar to constant weight to afford crude 6 (12.4 g—a higher yield would be achievable when omitting IPC sampling) with 98.7 area-% purity and a trans/cis ratio of 14. (R,R)-6 was obtained with >99.9% ee.

Specified Impurities: Cis-6 (6.5%), Trans-4 (0.2%), Trans-5 (0.4%)

Next, crude (R,R)-6 (12.4 g) was suspended in DCM (100 mL) and the slurry stirred for 2 h at 50° C. The suspension was cooled to 0° C. and stirred at this temperature for 1 h, filtered and the filter cake washed with ice-cold DCM (60 ml) in 3 portions to afford after drying (25° C., 10 mbar) pure 6 (11.0 g, 91% yield) with 99.8 area-% purity and a trans/cis ratio of 65. (R,R)-6 was obtained with >99.9% ee.

Specified Impurity: Cis-6 (1.52%)

Subsequently, (R,R)-6 (11.0 g) from above was dissolved in iPrOAc (88 ml) at 90° C. The colorless solution was cooled to 25° C. within 2 h whereby the product started to crystallize. The formed suspension was kept at 25° C. for 2 h and cooled to 0° C. within 30 min. The crystals were filtered and washed with ice-cold iPrOAc (30 ml) in 2 portions to afford after drying (25° C., 10 mbar) off white, crystalline 6 (9.0 g, 75% yield—a higher yield would be achievable when omitting IPC sampling during the hydrogenation run) with >99.9 area-% purity and a trans/cis ratio of 713. (R,R)-6 was obtained with >99.9% ee.

Specified Impurity: Cis-6 (0.14%)

TABLE 18

| | | 3 | | trans-4 | trans-5 | 6 | (R,R)-6 | 6 |
|---|---|---|---|---|---|---|---|---|
| ret [h] | conv [%] | [area-%] | [% ee] | [area-%] | [area-% | [area-%] | [% ee] | [trans/cis] |
| 2 | 89 | 87 | 95 | 0.4 | 0 | 0 | — | — |
| 4 | >99.9 | 95 | 93 | 4.5 | 0.1 | 0.2 | — | — |
| 23 | >99.9 | — | — | 0.2 | 0.4 | 98.1 | >99.9 | 14 |

Example 2.61

In a glove box under argon atmosphere, a 380 mL autoclave was charged with 1 (15.0 g, 59 mmol), 630 (45.1 mg, $5.9\times10^{-5}$ mol, S/C 1,000), 680 (11.5 mg, $1.2\times10^{-5}$ mol, S/C 5,000), DBU (179.3 mg, 1.2 mmol, S/B 50) and EtOH (300 mL). The autoclave was sealed and removed from the glove box, connected to a hydrogen line and pressurized with hydrogen gas to 70 bar and heated to 30° C. Under stirring, the hydrogenation was ran at a constant hydrogen pressure of 70 bar. After a total reaction time of 23 h (>99.9% conversion), the autoclave was vented and allowed to cool to room temperature. The reaction mixture was transferred with aid of EtOH (200 mL) from the autoclave into a 500 mL round bottomed flask and the orange reaction solution rotatory evaporated at 40° C./10 mbar to constant weight to afford crude 6 (13.2 g) with 99.4 area-% purity and a trans cis ratio of 18. (R,R)-6 was obtained with >99.9% ee.

Specified Impurities: Cis-6 (5.1%), Trans-5 (0.3%)

Next, crude (R,R)-6 (13.2 g) was suspended in iPrOAc (106 mL) and the slurry stirred for 2 h at 50° C. The suspension was cooled to 0° C. and stirred at this temperature for 1 h, filtered and the filter cake washed with ice-cold iPrOAc (60 ml) in 3 portions to afford after drying (25° C., 10 mbar) pure 6 (10.6 g, 83% yield) with 99.8 area-% purity and a trans cis ratio of 91. (R,R)-6 was obtained with >99.9% ee.

Specified Impurity: Cis-6 (1.1%)

Subsequently, (R,R)-6 (10.6 g) from above was dissolved in iPrOAc (85 ml) at 90° C. The colorless solution was cooled to 25° C. within 2 h whereby the product started to crystallize. The formed suspension was kept at 25° C. for 2 h and cooled to 0° C. within 30 min. The crystals were filtered and washed with ice-cold iPrOAc (30 ml) in 2 portions to afford after drying (25° C., 10 mbar) off-white, crystalline 6 (9.8 g, 77% yield) with >99.9 area-% purity and a trans cis ratio of 249. (R,R)-6 was obtained with >99.9% ee.

Specified Impurity: Cis-6 (0.41%)

Analytical Data for Trans-6

GC-MS ESI (m/z): 216.0 [M+]

NMR (400 MHz, DMSO) δ 7.27-7.42 (m, 4H), 5.21 (d, J=4.8 Hz, 1H), 4.69-4.82 (m, 1H), 4.48 (br d, J=4.6 Hz, 2H), 3.62-3.75 (m, 1H), 3.20-3.31 (m, 2H), 1.59-1.73 (m, 1H), 1.42 (ddd, J=13.9, 9.5, 2.2 Hz, 1H).

3. Preparation of (R,R)-6 Via Asymmetric Hydrogenation of (R)-3

Example 3.1

In a glove box under argon atmosphere, a 185 mL autoclave was charged with (R)-3 (1.00 g, 3.91 mmol, quality: 99.9% ee, 99.8 area-% purity), 680 (3.83 mg, $3.91\times10^{-6}$ mol, S/C 1,000) and DBU (59.5 mg, $3.91\times10^{-4}$ mol, S/B 10) and EtOH (20 mL). The autoclave was sealed and removed from the glove box, connected to a hydrogen line and pressurized with hydrogen gas to 70 bar and heated to 30° C. Under stirring, the hydrogenation was ran at a constant hydrogen pressure of 70 bar. Reaction samples were taken at different time points (see Table 19) to follow the progress of the reaction.

TABLE 19

| ret [h] | conv [%] | trans-4 [area-%] | trans-5 [area-%] | 6 [area-%] | (R,R)-6 [% ee] | 6 [trans/cis] |
|---|---|---|---|---|---|---|
| 1 | 46 | 14 | 7 | 0.8 | n.d. | — |
| 2 | 99.2 | 19 | 19 | 54 | 99.9 | 84 |
| 3 | >99.9 | 0.4 | 1.1 | 94 | 99.9 | 49 |
| 4 | >99.9 | 0 | 0.2 | 95 | 99.9 | 40 |

TABLE 19-continued

| ret [h] | conv [%] | trans-4 [area-%] | trans-5 [area-%] | 6 [area-%] | (R,R)-6 [% ee] | 6 [trans/cis] |
|---|---|---|---|---|---|---|
| 5 | >99.9 | 0 | 0 | 95.5 | 99.9 | 37 |
| 6 | >99.9 | 0 | 95.7 | 95.7 | 99.9 | 38 |

Example 3.2-3.3

In analogy to Example 3.1, 3 (0.25 g, 0.98 mmol) was hydrogenated in the presence of 680 (0.19 mg, $0.20\times10^{-6}$ mol, S/C 5,000) for 23 h in EtOH (4 mL) at 30° C. and the presence of DBU as base in amounts as listed in Table 20.

TABLE 20

| Exp | base | S/B | conv [%] | trans-4 [area-%] | trans-5 [area-%] | 6 [area-%] | (R,R)-6 [% ee] | 6 [trans/cis] |
|---|---|---|---|---|---|---|---|---|
| 3.2 | DBU | 20 | >99.9 | 0.3 | 0.1 | 94 | >99.9 | 39 |
| 3.3 | DBU | 50 | >99.9 | 0.1 | 0.1 | 97.2 | >99.9 | 36 |

Example 3.4

In a glove box under argon atmosphere, a 185 mL autoclave was charged with (R)-3 (6.0 g, 23.0 mmol, quality: 99.9% ee, 99.8 area-% purity) 680 (22.9 mg, $2.3\times10^{-5}$ mol, S/C 1,000) and DBU (71.2 mg, $4.7\times10^{-4}$ mol, S/B 50) and EtOH (120 mL). The autoclave was sealed and removed from the glove box, connected to a hydrogen line and pressurized with hydrogen gas to 70 bar and heated to 30° C. Under stirring, the hydrogenation was ran at a constant hydrogen pressure of 70 bar. After a total reaction time of 23 h (99.9% conversion), the autoclave was vented and allowed to cool to room temperature. The reaction mixture was transferred with aid of EtOH (20 mL) from the autoclave into a 250 mL round bottomed flask and the orange reaction solution rotatory evaporated at 40° C./10 mbar to constant weight to yield crude (R,R)-6 (5.2 g) with 98.7 area-% purity and a trans/cis ratio of 28. (R,R)-6 was obtained with >99.9% ee.

Specified Impurities: Cis-6 (3.40%), 3 (0.10%)

Next, crude (R,R)-6 (5.2 g) was suspended in iPrOAc (52 mL) and the slurry stirred for 2 h at 50° C. The suspension was cooled to 0° C. and stirred at this temperature for 1 h, filtered and the filter cake washed with ice-cold iPrOAc (30 ml) in 3 portions to afford after drying (25° C., 10 mbar) pure 6 (4.1 g, 81% yield) with 99.5 area-% purity and a trans/cis ratio of 125. (R,R)-6 was obtained with >99.9% ee.

Specified Impurity: Cis-6 (0.79%)

Subsequently, (R,R)-6 (4.1 g) from above was dissolved in iPrOAc (34 ml) at 90° C. The colorless solution was cooled to 25° C. within 2 h whereby the product started to crystallize. The formed suspension was kept at 25° C. for 2 h and cooled to 0° C. within 30 min. The crystals were filtered and washed with ice-cold iPrOAc (14 ml) in 2 portions to afford after drying (25° C., 10 mbar) off white, crystalline 6 (3.7 g, 73% yield) with >99.9 area-% purity and a trans/cis ratio of 586. (R,R)-6 was obtained with >99.9% ee.

Specified Impurity: Cis-6 (0.17%)

4. Preparation of (R,R)-6 Via Asymmetric Hydrogenation of (R,R)-5

Example 4.1

In a glove box under argon atmosphere, a 185 mL autoclave was charged with (R,R)-5 (1.00 g, 4.71 mmol; quality: 99.9% ee, 99.9 area-% purity), 680 (4.62 mg, $4.71\times10^{-6}$ mol, S/C 1,000), DBU (71.7 mg, $4.71\times10^{-4}$ mol, S/B 10) and EtOH (20 mL). The autoclave was sealed and removed from the glove box, connected to a hydrogen line and pressurized with hydrogen gas to 70 bar and heated to 30° C. Under stirring, the hydrogenation was ran at a constant hydrogen pressure of 70 bar. A reaction sample was taken at different time points (see Table 21) to follow the progress of the reaction.

TABLE 21

| rct [h] | conv [%] | 6 [area-%] | (R,R)-6 [% ee] | 6 [trans/cis] |
|---|---|---|---|---|
| 1 | 90 | 82 | 99.9 | >100 |
| 2 | >99.9 | 98.2 | 99.9 | >100 |

Example 4.2

In analogy to Example 4.1, (R,R)-5 (0.25 g, 1.18 mmol; quality: 99.9% ee, 99.9 area-% purity) was hydrogenated in the presence of 680 (0.23 mg, $2.36\times10^{-7}$ mol, S/C 5,000) and DBU (9.0 mg, $0.59\times10^{-4}$ mol, S/B 20) in EtOH (5 mL) to yield after 20 h at 30° C. and an initial hydrogen pressure of 70 bar crude (R,R)-6 with 96.7% purity and >99.9% ee (99% conversion; trans cis ratio>100)

5. Preparation of (R,R)-8 Via Asymmetric Hydrogenation of 7

Examples 5.1

In a glove box under argon atmosphere, a 35 mL autoclave was charged with 7 (250 mg, 1.1 mmol), 680 (1.1 mg, $1.1\times10^{-6}$ mol, S/C 1,000), KOtBu (12.1 mg, $1.1\times10^{-4}$ mol, S/B 10) and EtOH (5 mL). The autoclave was sealed and removed from the glove box, connected to a hydrogen line and pressurized with hydrogen gas to 70 bar and heated to 30° C. Under stirring, the hydrogenation was ran at a constant hydrogen pressure of 70 bar. After a total reaction time of 20 h, the autoclave was vented and allowed to cool to room temperature. The reaction mixture was transferred with aid of EtOH (5 mL) from the autoclave into a 50 mL round bottomed flask and the orange reaction solution rotatory evaporated at 40° C./10 mbar to constant weight to yield crude trans-8 (presumable major enantiomer: (R,R)-8, 245 mg) with >95% LC/MS purity.

Analytical Data for Trans-8

GC-MS ESI (m/z): 182.1 [M+]

$^1$H-NMR ($CDCl_3$, 600 MHz): δ ppm 7.30-7.42 (m, 1H), 7.28-7.42 (m, 3H), 5.03 (br d, J=3.8 Hz, 1H), 3.98 (br s, 1H), 3.44-3.64 (m, 2H), 3.03-3.44 (m, 2H), 2.38-2.86 (m, 1H), 1.72-2.03 (m, 3H)

$^{13}$C-NMR ($CDCl_3$, 151 MHz): δ ppm 144.2, 128.5, 127.5, 125.5, 71.4, 69.4, 66.8, 41.0 ppm

The invention claimed is:

1. Process for the preparation of a chiral triol of formula I

I

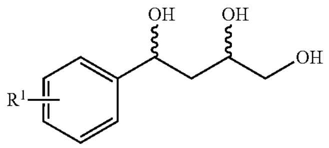

wherein $R^1$ is hydrogen or halogen and denotes either a dashed bond (a) or a wedged bond (b)

a)  b)

comprising the asymmetric hydrogenation of a ketone compound of formula IIa

IIa

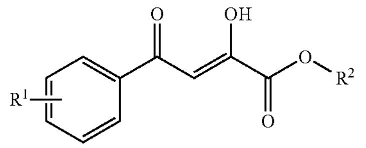

wherein $R^1$ is hydrogen or halogen and $R^2$ is $C_{1-6}$-alkyl;

with hydrogen in the presence of an iridium spiro-pyridylamidophosphine catalyst (Ir-SpiroPAP catalyst) of the formula IIIa or IIIb, or enantiomers thereof, IIIa

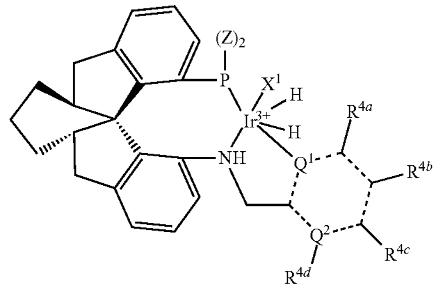

IIIb

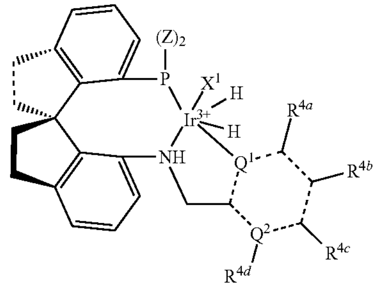

wherein $R^{4a}$, $R^{4b}$, $R^{4c}$ and $R^{4d}$ independently of each other are hydrogen or $C_{1-6}$-alkyl;

the dotted ring signifies an aromatic ring when $Q^1$ is nitrogen and $Q^2$ is carbon and the dotted ring signifies a cycloalkane ring wherein $Q^1$ and $Q^2$ are sulfur;

$X^1$ is either a coordinated ligand or a counter anion selected from halogen, $C_{1-6}$-alkoxy, tetrahalogeno borate, hexahalogenoborate, tetrakis(3,5-bis(trihalogeno-$C_{1-6}$-alkyl)phenyl)borate, acetylacetonate, hexahalogenophosphate, p-tolylsulfonate (OTs) or trihalogeno methanesulfonate and Z is phenyl, optionally substituted by one or more groups selected from $C_{1-8}$-alkyl, $C_{1-8}$-halogenalkyl or phenyl; $C_{3-8}$-cycloalkyl, optionally substituted by one or more $C_{1-8}$-alkyl groups or di-$C_{1-8}$-alkyl phosphinyl.

2. Process of claim 1, wherein the Ir-SpiroPAP catalyst is selected from the compounds IIIa or IIIb, or enantiomers thereof, wherein $R^{4a}$, $R^{4b}$, $R^{4c}$ and $R^{4d}$ independently of each other are hydrogen or $C_{1-4}$-alkyl;

the dotted ring signifies an aromatic ring when $Q^1$ is nitrogen and $Q^2$ is carbon and the dotted ring signifies a cycloalkane ring wherein $Q^1$ and $Q^2$ are sulfur;

$X^1$ is either a coordinated ligand or a counter anion selected from halogen, methoxy, tetrafluoroborate (BF4), hexafluoroborate (BF6), tetrakis(3,5-bis(trifluoromethyl) phenyl)borate (barf), acetylacetonate (acac), hexafluorophosphate (PF6), p-tolylsulfonate (OTs) or trifluoromethanesulfonate (OTf) and;

Z is phenyl, optionally substituted by one or more groups selected from $C_{1-6}$-alkyl, $C_{1-4}$-halogenalkyl or phenyl or is $C_{4-7}$-cycloalkyl.

3. Process of claim 1, wherein the Ir-SpiroPAP catalyst is selected from the compounds IIIa or IIIb, or enantiomers thereof $R^{4a}$, $R^{4b}$, $R^{4c}$ and $R^{4d}$ independently of each other are hydrogen or $C_{1-4}$-alkyl;

the dotted ring signifies an aromatic ring when $Q^1$ is nitrogen and $Q^2$ is carbon and the dotted ring signifies a cycloalkane ring wherein $Q^1$ and $Q^2$ are sulfur;

$X^1$ is halogen;

Z is phenyl, optionally substituted by one or two groups selected from $C_{1-6}$-alkyl, $C_{1-4}$-halogenalkyl or phenyl or is cyclopentyl or cyclohexyl.

4. Process of claim 1, wherein the Ir-SpiroPAP catalyst is selected from the compounds IIIc

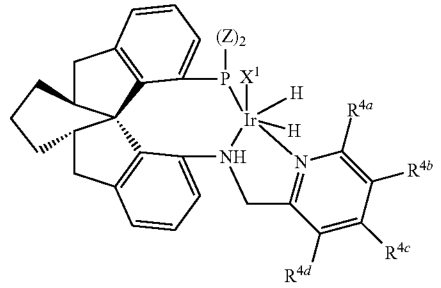

IIId

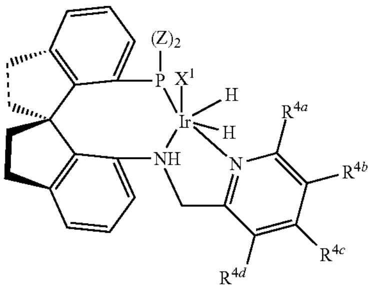

-continued

IIIe

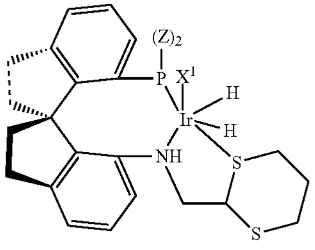

wherein;

$R^{4a}$, $R^{4b}$, $R^{4c}$ and $R^{4d}$ independently of each other are hydrogen or $C_{1-4}$-alkyl;

$X^1$ is halogen;

Z is phenyl optionally substituted by one or two groups selected from $C_{1-6}$-alkyl, $C_{1-4}$-halogenalkyl or phenyl or is cyclopentyl or cyclohexyl.

5. Process of claim 1, wherein the asymmetric hydrogenation is performed in the presence of an organic solvent and a base at a hydrogen pressure of 5 bar to 100 bar and at a reaction temperature of 10° C. to 90° C.

6. Process of claim 1, wherein the organic solvent is an aliphatic alcohol, a halogen substituted alcohol, an ether or an aromatic solvent or is a mixture thereof.

7. Process of claim 1, wherein the base is an inorganic base selected from alkali or earth alkali—carbonates or—hydrogen carbonates or phosphates or hydrogenphosphates or dihydrogenphosphates or acetates or formates or organic bases selected from amines, alkali alcoholates or amidines.

8. Process of claim 1, wherein the substrate to catalyst ratio is selected in a range of 100 to 10,000.

9. Process of claim 1, wherein the Ir-SpiroPAP catalyst of formula IIIa or IIIb is prepared in situ in the course of the asymmetric hydrogenation reaction by bringing together a Iridium-pre catalyst complex with a spiro-pyridylamidophosphine ligand of the formula VIa

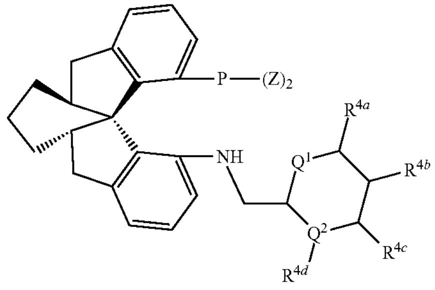

VIb

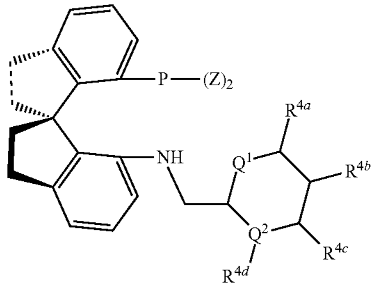

wherein $R^{4a}$, $R^{4b}$, $R^{4c}$ and $R^{4d}$, $Q^1$ and $Q^2$ and Z have the meanings as outlined above.

10. Process of claim 9, wherein the Iridium-pre catalyst complex is selected from $[Ir(cod)_2]BF_4$, $[IrCl(COD)]_2$, [Ir(acac)(COD)], $[Ir(OMe)(COD)]_2$, $[Ir(cod)_2]BARF$, $[Ir(cod)_2]PF6$.

11. Process of claim 1, wherein the asymmetric hydrogenation of the ketone of formula IIa in a first step is performed in the presence of the Ir-PEN catalyst of formula IVa or IVb, or enantiomers thereof, IVa

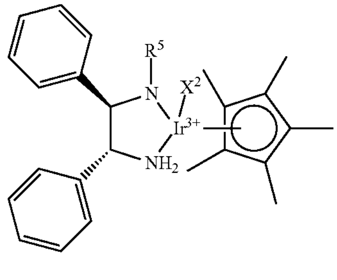

IVb

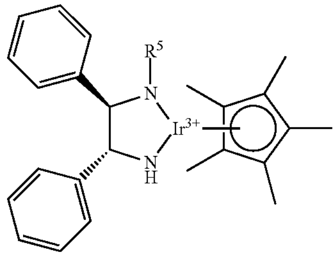

wherein, $R^5$ is $C_{1-6}$-alkylsulfonyl wherein the alkyl group is optionally substituted with one or more halogen atoms; with a 7,7-dimethyl-2-oxobicyclo[2.2.1] heptane-1-yl group or phenyl sulfonyl, wherein the phenyl group is optionally substituted by one or more $C_{1-6}$-alkyl groups and $X^2$ is either a coordinated ligand or a counter anion selected from a $C_{1-6}$-alkylsulfonyloxy group which is optionally substituted with one or more halogen, atoms; from halogen, $C_{1-6}$-alkoxy, tetrahalogenoborate, hexahalogenoborate, tetrakis(3,5-bis(trihalogeno-$C_{1-6}$-alkyl)phenyl)borate, acetylacetonate, hexahalogenophosphine, p-tolylsulfonate (OTs) or trihalogenomethanesulfonate;

to form the ketone of formula IIb,

IIb

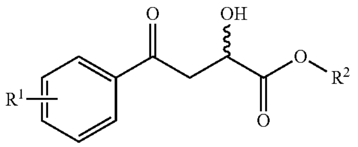

wherein $R^1$ and $R^2$ are as above, and in a subsequent step the ketone of formula IIb is further subjected to an asymmetric hydrogenation in the presence of an Ir-SpiroPAP catalyst of the formula IIIa or IIIb, or enantiomers thereof, to form the chiral triol of formula I.

12. Process of claim 11, wherein $R^5$ is methylsulfonyl, trifluoromethylsulfonyl, 7,7-dimethyl-2-oxobicyclo[2.2.1] heptane-1-yl; tolylsulfonyl or 1,3,5-tri-i-propylphenyl sulfonyl;

$X^2$ is either a coordinated ligand or a counter anion selected from a methylsulfonyloxy group which is optionally substituted with one or more fluoro atoms; from halogen, methoxy, tetrafluoroborate (BF4), hexafluoroborate (BF6), tetrakis (3,5-bis(trifluoromethyl)phenyl)borate (barf), acetylacetonate (acac), hexafluorophosphine (PF6), p-tolylsulfonate (OTs) or trifluoromethanesulfonate (OTf.

13. Process of claim 11, wherein the iridium-phenylendiamine catalyst (Ir-PEN catalyst) are of the formula IVa, or enantiomers thereof, wherein, $R^5$ is methylsulfonyl, trifluoromethylsulfonyl, 7,7-dimethyl-2-oxobicyclo [2.2.1] heptane-1-yl; tolylsulfonyl or 1,3,5-tri-i-propylphenyl sulfonyl;

$X^2$ is a trifluoromethylsulfonyl oxy group; or are of the formula IVb, or enantiomers thereof, wherein, $R^5$ is methylsulfonyl, trifluoromethylsulfonyl, 7,7-dimethyl-2-oxobicyclo [2.2.1] heptane-1-yl; tolylsulfonyl or 1,3,5-tri-i-propylphenyl sulfonyl.

14. Process of claim 11, wherein the asymmetric hydrogenation of the ketone of formula IIa is performed in the presence of an organic solvent at a hydrogen pressure of 5 bar to 100 bar and at a reaction temperature of 10° C. to 90° C.

15. Process of claim 14, wherein the organic solvent is an aliphatic alcohol, a halogen substituted alcohol, an ether or an aromatic solvent or is a mixture thereof.

16. Process of claim 14, wherein the substrate to catalyst ratio is selected in a range of 100 to 1000.

17. Process of claim 11, wherein the asymmetric hydrogenation of the ketone of formula IIa takes place in the presence of a mixture of an Ir-Spiro PAP catalyst of the formula IIIa or IIIb, or of an enantiomer thereof, and an Ir-PEN catalyst of the formula IVa or IVb, or of an enantiomer thereof.

18. Process of claim 17 wherein the reaction is performed in the presence of an organic solvent and a base at a hydrogen pressure of 5 bar to 100 bar and at a reaction temperature of 10° C. to 90° C.

19. Process of claim 18, wherein the organic solvent is an aliphatic alcohol, a halogen substituted alcohol, an ether or an aromatic solvent or is a mixture thereof.

20. Process of claim 18, wherein the base is an inorganic base selected from alkali or earth alkali—carbonates or—hydrogen carbonates or phosphates or hydrogenphosphates or dihydrogenphosphates or acetates or formates or organic bases selected from amines, alkali alcoholates or amidines.

21. Process of claim 17, wherein the substrate to Ir-PEN catalyst ratio is selected in a range of 100 to 10000, and the substrate to Ir-Spiro PAP catalyst ratio is selected in a range of 100 to 10000.

22. Process of claim 1, wherein the intermediates in the asymmetric hydrogenation of the ketone of formula IIa to the chiral triol of formula I of the formula IIb

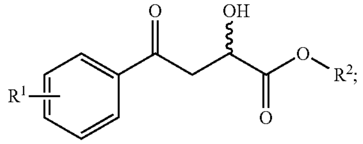

IIc

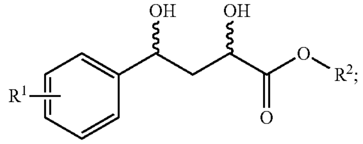

IId

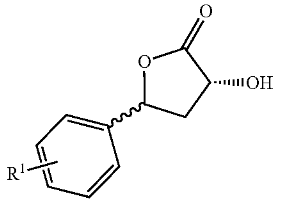

wherein $R^1$ and $R^2$ are as above, are individually isolated and individually be subjected to the asymmetric hydrogenation in the presence of an Ir-Spiro PAP catalyst of the formula IIIa or IIIb.

23. Process of claim 1, wherein the chiral triol has the formula Ia

Ia

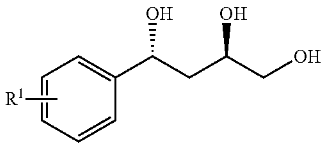

$R^1$ is hydrogen or halogen.

24. Process of claim 23, wherein $R^1$ is halogen.

25. Process of claim 1, wherein the chiral triol has the formula Ib

Ib

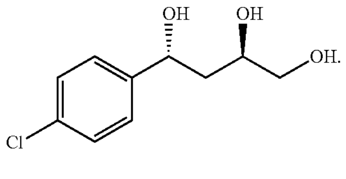

* * * * *